US010039285B2

(12) United States Patent
Savage et al.

(10) Patent No.: US 10,039,285 B2
(45) Date of Patent: Aug. 7, 2018

(54) CERAGENIN PARTICULATE MATERIALS AND METHODS FOR MAKING SAME

(71) Applicant: BRIGHAM YOUNG UNIVERSITY, Provo, UT (US)

(72) Inventors: Paul B. Savage, Mapleton, UT (US); Carl Genberg, Las Vegas, NV (US)

(73) Assignee: Brigham Young University, Provo, UT (US)

(*) Notice: Subject to any disclaimer, the term of this patent is extended or adjusted under 35 U.S.C. 154(b) by 0 days.

(21) Appl. No.: 14/398,094

(22) PCT Filed: Mar. 13, 2013

(86) PCT No.: PCT/US2013/030955
§ 371 (c)(1),
(2) Date: Oct. 30, 2014

(87) PCT Pub. No.: WO2013/165574
PCT Pub. Date: Nov. 7, 2013

(65) Prior Publication Data
US 2015/0093423 A1  Apr. 2, 2015

Related U.S. Application Data

(60) Provisional application No. 61/641,771, filed on May 2, 2012.

(51) Int. Cl.
| | |
|---|---|
| *B02C 23/12* | (2006.01) |
| *A61K 9/14* | (2006.01) |
| *A01N 45/00* | (2006.01) |
| *A01N 55/00* | (2006.01) |
| *A01N 55/08* | (2006.01) |
| *B02C 23/24* | (2006.01) |
| *A61K 8/02* | (2006.01) |
| *A01N 25/08* | (2006.01) |
| *A01P 1/00* | (2006.01) |

(52) U.S. Cl.
CPC .............. *A01N 45/00* (2013.01); *A01N 55/00* (2013.01); *A01N 55/08* (2013.01); *B02C 23/12* (2013.01); *B02C 23/24* (2013.01)

(58) Field of Classification Search
None
See application file for complete search history.

(56) References Cited

U.S. PATENT DOCUMENTS

| | | | |
|---|---|---|---|
| 4,248,236 A | 2/1981 | Linder | |
| 4,296,206 A | 10/1981 | Simons | |
| 4,661,341 A | 4/1987 | Benedict et al. | |
| 4,723,950 A | 2/1988 | Lee | |
| 4,765,855 A | 8/1988 | Geoffroy-Dechaume et al. | |
| 4,842,593 A | 6/1989 | Jordan et al. | |
| 4,972,848 A | 11/1990 | DiDomenico | |
| 5,025,754 A | 6/1991 | Plyler | |
| 5,286,479 A | 2/1994 | Garlich et al. | |
| 5,310,545 A | 5/1994 | Eisen | |
| 5,356,630 A | 10/1994 | Laurencin et al. | |
| 5,364,650 A | 11/1994 | Guthery | |
| 5,380,839 A | 1/1995 | McCall et al. | |
| 5,552,057 A | 9/1996 | Hughes et al. | |
| 5,624,704 A | 4/1997 | Darouiche et al. | |
| 5,721,359 A | 2/1998 | Dunn et al. | |
| 5,763,430 A | 6/1998 | Zasloff | |
| 6,117,332 A | 9/2000 | Hatch et al. | |
| 6,228,393 B1 | 5/2001 | DiCosmo et al. | |
| 6,329,488 B1 | 12/2001 | Terry et al. | |
| 6,350,738 B1 | 2/2002 | Savage et al. | |
| 6,486,148 B2 | 11/2002 | Savage et al. | |
| 6,562,318 B1 | 5/2003 | Filler | |
| 6,582,713 B2 | 6/2003 | Newell et al. | |
| 6,673,771 B1 | 1/2004 | Greene et al. | |
| 6,767,904 B2 | 7/2004 | Savage et al. | |
| 6,773,717 B1 | 8/2004 | Winstrom | |
| 6,803,066 B2 | 10/2004 | Traeder | |
| 6,872,306 B2 | 3/2005 | Knapp et al. | |
| 6,939,376 B2 | 9/2005 | Shulze et al. | |
| 7,282,214 B2 | 10/2007 | Wilcox et al. | |
| 7,381,439 B2 | 6/2008 | Hilgren et al. | |
| 7,598,234 B2 | 10/2009 | Savage et al. | |
| 7,659,061 B2 | 2/2010 | Hendl et al. | |

(Continued)

FOREIGN PATENT DOCUMENTS

| | | |
|---|---|---|
| CN | 101378761 | 3/2009 |
| EP | 1208844 | 5/2002 |

(Continued)

OTHER PUBLICATIONS

U.S. Appl. No. 14/694,028, filed Apr. 23, 2015, Beus et al.
U.S. Appl. No. 14/750,928, filed Jun. 25, 2015, Genberg et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/873,013, filed Oct. 1, 2015, Savage et al.
U.S. Appl. No. 14/875,953, filed Oct. 6, 2015, Savage.
U.S. Appl. No. 14/926,738, filed Oct. 29, 2015, Vazquez et al.
Berge et al., "Pharmaceutical Salts", Journal of Pharmaceutical Sciences, Jan. 1977, vol. 66, No. 1, pp. 1-19.

(Continued)

*Primary Examiner* — Robert T. Crow
*Assistant Examiner* — John P Nguyen
(74) *Attorney, Agent, or Firm* — Workman Nydegger

(57) ABSTRACT

Particulate ceragenin materials may be manufactured by (i) providing a ceragenin feed material comprised of ceragenin molecules, each having a sterol backbone and a plurality cationic groups attached thereto; (ii) fracturing the ceragenin feed material in a milling apparatus to produce a ceragenin particulate material having a particle size distribution with a median particle size in a range from 5 nm to 20 μm; and (iii) during fracturing, maintaining the ceragenin feed with a moisture content of less than or equal to 10% by weight.

19 Claims, 27 Drawing Sheets

(56) References Cited

U.S. PATENT DOCUMENTS

| | | | |
|---|---|---|---|
| 7,754,705 | B2 | 7/2010 | Savage et al. |
| 7,854,941 | B2 | 12/2010 | Urban et al. |
| 7,993,903 | B2 | 8/2011 | Hayakawa et al. |
| 8,211,879 | B2 | 7/2012 | Savage et al. |
| 8,529,681 | B1 | 9/2013 | Hibbs et al. |
| 8,623,416 | B2 | 1/2014 | Zasloff et al. |
| 8,691,252 | B2 | 4/2014 | Savage |
| 8,784,857 | B2 | 7/2014 | Savage |
| 8,787,857 | B2 | 7/2014 | Savage |
| 9,527,883 | B2 | 12/2016 | Savage et al. |
| 2002/0091278 | A1 | 7/2002 | Savage et al. |
| 2003/0018306 | A1 | 1/2003 | Bucay-Couto et al. |
| 2003/0099717 | A1 | 5/2003 | Cabrera |
| 2004/0009227 | A1 | 1/2004 | Yao |
| 2004/0011358 | A1 | 1/2004 | Smaldone et al. |
| 2004/0018154 | A1 | 1/2004 | Pan |
| 2004/0058974 | A1 | 3/2004 | Courtney et al. |
| 2004/0071781 | A1 | 4/2004 | Chattopadhyay et al. |
| 2004/0121003 | A1* | 6/2004 | Chickering, III ...... A61K 9/145 424/465 |
| 2004/0170563 | A1 | 9/2004 | Meade |
| 2004/0259445 | A1 | 12/2004 | Hilfenhaus et al. |
| 2005/0032765 | A1 | 2/2005 | Savage et al. |
| 2005/0075321 | A1 | 4/2005 | Ahlem et al. |
| 2005/0244468 | A1 | 11/2005 | Huang et al. |
| 2005/0267051 | A1 | 12/2005 | Lee et al. |
| 2006/0035192 | A1* | 2/2006 | Coles ................ A23B 4/031 432/58 |
| 2006/0062742 | A1 | 3/2006 | Davis et al. |
| 2006/0147389 | A1* | 7/2006 | Staniforth ........... A61K 9/0073 424/46 |
| 2006/0269485 | A1 | 11/2006 | Friedman et al. |
| 2007/0106393 | A1 | 5/2007 | Miles et al. |
| 2007/0134292 | A1 | 6/2007 | Suokas et al. |
| 2007/0190066 | A1 | 8/2007 | Savage et al. |
| 2007/0190067 | A1 | 8/2007 | Savage et al. |
| 2007/0190558 | A1 | 8/2007 | Savage et al. |
| 2008/0124376 | A1 | 5/2008 | Pruitt et al. |
| 2008/0174035 | A1 | 7/2008 | Winterton |
| 2008/0188819 | A1 | 8/2008 | Kloke et al. |
| 2008/0279944 | A1 | 11/2008 | Sawhney |
| 2009/0016973 | A1 | 1/2009 | Ratcliff et al. |
| 2009/0054295 | A1 | 2/2009 | Vicari et al. |
| 2009/0068122 | A1 | 3/2009 | Pilch et al. |
| 2009/0099531 | A1 | 4/2009 | Griesbach, III |
| 2009/0252781 | A1 | 10/2009 | Sawhney et al. |
| 2009/0324517 | A1 | 12/2009 | Kline |
| 2010/0022481 | A1 | 1/2010 | Wang et al. |
| 2010/0092398 | A1 | 4/2010 | Reynolds |
| 2010/0209497 | A1 | 8/2010 | Thornthwaite |
| 2010/0226884 | A1 | 9/2010 | Chang et al. |
| 2010/0310478 | A1 | 12/2010 | Fitzgerald et al. |
| 2010/0330086 | A1 | 12/2010 | Savage et al. |
| 2011/0091376 | A1 | 4/2011 | Savage et al. |
| 2011/0123624 | A1 | 5/2011 | Zasloff |
| 2011/0135742 | A1 | 6/2011 | Kim et al. |
| 2011/0230589 | A1 | 9/2011 | Maggio et al. |
| 2012/0088733 | A1 | 4/2012 | Kim et al. |
| 2012/0107382 | A1 | 5/2012 | Savage |
| 2013/0022651 | A1 | 1/2013 | Savage et al. |
| 2013/0053507 | A1 | 2/2013 | Savage |
| 2013/0234842 | A1 | 9/2013 | Genberg et al. |
| 2013/0236619 | A1 | 9/2013 | Savage |
| 2013/0243823 | A1 | 9/2013 | Genberg et al. |
| 2013/0243840 | A1 | 9/2013 | Savage et al. |
| 2013/0245760 | A1 | 9/2013 | Savage et al. |
| 2013/0280312 | A1 | 10/2013 | De Szalay |
| 2013/0280391 | A1 | 10/2013 | Savage |
| 2014/0107090 | A1 | 4/2014 | Beus et al. |
| 2014/0194401 | A1 | 7/2014 | Genberg et al. |
| 2014/0219914 | A1 | 8/2014 | Govindan et al. |
| 2014/0271761 | A1 | 9/2014 | Savage et al. |
| 2014/0274913 | A1 | 9/2014 | Savage et al. |
| 2014/0305461 | A1 | 10/2014 | Pimenta et al. |
| 2014/0315873 | A1 | 10/2014 | Beus et al. |
| 2014/0363780 | A1 | 12/2014 | Vazquez et al. |
| 2014/0369941 | A1 | 12/2014 | Vazquez et al. |
| 2015/0140063 | A1 | 5/2015 | Savage |
| 2015/0203527 | A1 | 7/2015 | Savage |
| 2015/0239928 | A1 | 8/2015 | Savage |
| 2015/0258121 | A1 | 9/2015 | Darien et al. |
| 2015/0258122 | A1 | 9/2015 | Beus et al. |
| 2015/0258123 | A1 | 9/2015 | Savage et al. |
| 2016/0193232 | A1 | 3/2016 | Beus et al. |
| 2016/0199390 | A1 | 3/2016 | Beus et al. |
| 2016/0311850 | A1 | 10/2016 | Savage et al. |

FOREIGN PATENT DOCUMENTS

| | | | |
|---|---|---|---|
| EP | 1219631 | 7/2002 | |
| EP | 1250849 | 10/2002 | |
| JP | 02014741 | 1/1990 | |
| JP | 06153779 | 6/1994 | |
| JP | 07501826 | 2/1995 | |
| JP | 09248454 | 9/1997 | |
| JP | 2002505292 | 2/2002 | |
| JP | 2002255771 | 9/2002 | |
| JP | 2002534532 | 10/2002 | |
| JP | 2002538093 | 11/2002 | |
| JP | 2004506645 | 3/2004 | |
| JP | 2010533051 | 10/2010 | |
| JP | 2011527702 | 11/2011 | |
| JP | 2014500741 | 1/2014 | |
| JP | 20105380741 | 1/2014 | |
| WO | 0341951 | 11/1989 | |
| WO | WO1993001829 | 2/1993 | |
| WO | WO 1995024415 | 9/1995 | |
| WO | WO-9632149 A1 * | 10/1996 | ........... A61K 9/0075 |
| WO | WO9827106 | 6/1998 | |
| WO | WO 1999044616 | 9/1999 | |
| WO | WO 2000042058 | 7/2000 | |
| WO | WO0214342 | 2/2002 | |
| WO | WO 2002014342 | 2/2002 | |
| WO | WO2002067979 | 9/2002 | |
| WO | WO 2003015757 | 2/2003 | |
| WO | WO 03090799 | 11/2003 | |
| WO | WO2004082588 | 9/2004 | |
| WO | WO 2004112852 | 12/2004 | |
| WO | WO 2007089903 | 8/2007 | |
| WO | WO 2007089906 | 8/2007 | |
| WO | WO2007089907 | 8/2007 | |
| WO | WO 2007134176 | 11/2007 | |
| WO | WO 2008038965 | 4/2009 | |
| WO | WO2009144708 | 12/2009 | |
| WO | WO2010006192 | 1/2010 | |
| WO | WO 2010036427 | 4/2010 | |
| WO | WO 2010062562 | 6/2010 | |
| WO | WO2011066260 | 6/2011 | |
| WO | CN 102172356 | 9/2011 | |
| WO | WO 2011109704 | 9/2011 | |
| WO | WO 2012061651 | 5/2012 | |
| WO | WO2013029055 | 2/2013 | |
| WO | WO2013029059 | 2/2013 | |
| WO | WO-2013104265 A1 * | 3/2013 | ........... A61K 31/575 |
| WO | WO 2013109236 | 7/2013 | |
| WO | WO-2014062960 A1 * | 4/2014 | ........... A61K 31/575 |

OTHER PUBLICATIONS

Clara et al., "Preclinical evaluation of magainin—A as a contraceptive antimicrobial agent", Fertility and Sterility 81 (5), pp. 1357-1365, 2004.

International Search Report for PCT Application No. PCT/US2014/034986 dated Aug. 28, 2014.

International Search Report for PCT Application No. PCT/US2013/065510, dated Apr. 30, 2015.

International Search Report for PCT Application No. PCT/US2015/020166 dated Sep. 2, 2015.

International Search Report for PCT Application No. PCT/US2015/038029 dated Sep. 29, 2015.

Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).

(56) References Cited

OTHER PUBLICATIONS

Zanger et al., "Structure-Activity Relationship and Drug Design", Remington's Pharmaceutical Sciences, Chapter 27, 16th Edition, 1980, pp. 420-425.
Lai et el., "Ceragenins: Cholic Acid-Based Mimics of Antimicrobial Peptides", Oct. 21, 2008, pp. 1233-1240, vol. 41, No. 10, Accounts of Chemical Research.
Lai et al., "Controlled Release of a Bactericidal Ceragenin-Polymer Conjugate", Sep. 27, 2006, p. 1, 46$^{th}$ Annual Interscience Conference on Antimicrobial Agents and Chemotherapy.
Savage et al., "Use of a Ceragenin-Based Colonization of Urinary Catheters", Oct. 26, 2008, p. 1, 46$^{th}$ Annual Interscience Conference on Antimicrobial Agents and Chemotherapy.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Suzuki et al., "Molecular Genetics of Plant Sterol Backbone Synthesis", 2007; Lipids; 42: 47-54.
Van Den Bogaard et al., "Antibiotic Usage in Animals: Impact on Bacterial Resistance and Public Health"; 1999; Drugs; 58 (4): 589-607.
U.S. Appl. No. 13/615,244, filed Sep. 13, 2012, Office Action dated Jan. 16, 2015.
U.S. Appl. No. 14/257,776, filed Apr. 21, 2014, Restriction Requirement dated Jan. 22, 2015.
U.S. Appl. No. 14/364,283, filed Jul. 29, 2014, Office Action dated Feb. 11, 2015.
U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.
U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/257,776, filed Apr. 21, 2014, Office Action dated Apr. 16, 2015.
U.S. Appl. No. 13/783,007, filed Mar. 1, 2013, Savage.
U.S. Appl. No. 14/288,126, filed May 27, 2014, Savage et al.
U.S. Appl. No. 14/339,342, filed Jul. 23, 2014, Vazquez et al.
U.S. Appl. No. 14/341,304, filed Jul. 25, 2014, Savage et al.
U.S. Appl. No. 14/364,283, filed Jul. 29, 2014, Vazquez et al.
U.S. Appl. No. 14/515,858, filed Oct. 16, 2014, Savage et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/o10062704/suppl file/o10062704 sl.pdf.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/0475485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
P. B. Savage, et al., "Thin Films Containing Ceragenins Prevent Biofilm Formation on Endotracheal Tubes", 9th International Federation of Infection Control Congress, Oct. 14, 2008, pp. 1-1.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld, et al., "Cow-specific treatment of clinical mastitis: an economic approach", Journal of Dairy Science vol. 94, Jan. 2011, pp. 174-188.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
U.S. Appl. No. 13/000,010, filed Dec. 17, 2012, Restriction Requirement dated Dec. 4, 2012.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.

(56) References Cited

OTHER PUBLICATIONS

U.S. Appl. No. 13/288,892, filed Nov. 3, 2011, Notice of Allowance dated Nov. 29, 2013.
U.S. Appl. No. 13/288,902, filed Nov. 3, 2011, Restriction Requirement dated Jun. 21, 2012.
U.S. Appl. No. 13/288,902, filed Nov. 3, 2011, Office Action dated Nov. 7, 2012.
U.S. Appl. No. 13/288,902, filed Nov. 3, 2011, Notice of Allowance dated Aug. 9, 2013.
U.S. Appl. No. 13/554,930, filed Jul. 20, 2012, Office Action dated Jul. 11, 2014.
U.S. Appl. No. 13/554,957, filed Jul. 20, 2012, Office Action dated Apr. 1, 2014.
U.S. Appl. No. 13/554,957, filed Jul. 20, 2012, Notice of Allowance dated Aug. 1, 2014.
U.S. Appl. No. 13/594,608, filed Aug. 24, 2012, Office Action dated Jan. 30, 2014.
U.S. Appl. No. 13/594,612, filed Aug. 24, 2012, Office Action dated May 15, 2014.
U.S. Appl. No. 13/615,324, filed Sep. 13, 2012, Office Action dated Jan. 30, 2014.
U.S. Appl. No. 13/783,131, filed Mar. 1, 2013, Office Action dated Oct. 23, 2014.
U.S. Appl. No. 14/056,122, filed Oct. 17, 2013, Office Action dated Sep. 3, 2014.
U.S. Appl. No. 15/135,969, filed Apr. 22, 2016, Savage et al.
U.S. Appl. No. 15/270,876, filed Sep. 20, 2016, Genberg et al.
U.S. Appl. No. 15/333,514, filed Oct. 25, 2016, Vazquez et al.
U.S. Appl. No. 15/454,135, filed Mar. 9, 2017, Savage et al.
U.S. Appl. No. 15/406,667, filed Jan. 16, 2017, Savage.
U.S. Appl. No. 15/481,884, filed Apr. 7, 2017, Savage.
U.S. Appl. No. 15/585,632, filed May 3, 2017, Savage et al.
Bush, "Staphylococcal Infections", Merck Manuals Professional Edition, http://www.merckmanuals.com/professional/infectious-diseases/gram-postive-cocci/staphylcoccal-infectons.
Cipolla et al., "Inhaled antibiotics to treat lung infection", Pharm Pat Anal., Sep. 2013.
Elder et al., "The Utility of Sulfonate Salts in Drug Development", Journal of Pharmaceutical Sciences 99(7): 2948-2961.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667-676, 1954.
Pycock, "The Dirty Mare", https://www.equine-reproduction.com/articles/DirtyMare.shtml, 2003.
Survey Research on Behcet's Disease, 2005 to 2007 Comprehensive Survey Reports, 2008, pp. 34-39.
U.S. Appl. No. 15/895,848, filed Feb. 13, 2018, Genberg et al.
U.S. Appl. No. 15/926,534, filed Mar. 20, 2018, Savage.
U.S. Appl. No. 15/926,577, filed Mar. 20, 2018, Savage et al.
BASF, Pluronic® Block Copolymer NF Grades (Poloxamer NF Grades), Technical Bulletive (2004).
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Food definition, Merriam Webster, https://www.merriam-webster.com/dictionary/food, Accessed Feb. 12, 2018.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
Papo et al., "Host peptides as new weapons in cancer treatment", CMLS Cell. Mol. Life Sci. 62 (2005), 784-790.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.

* cited by examiner

CERAGENIN PARTICULATE MATERIALS AND METHODS FOR MAKING SAME

GOVERNMENT LICENSE RIGHTS

This invention was made with government support under Grant Number AR057185 awarded by the National Institutes of Health. The government has certain rights in the invention.

The subject matter described herein was in-part made possible by support from the Department of Veterans Affairs. The government has certain rights in the invention.

BACKGROUND OF THE INVENTION

1. Field of the Invention

The invention is generally in the field of cationic steroidal anti-microbial compounds that mimic anti-microbial peptides and methods for making particulates of these compounds.

2. Related Technology

Ceragenin compounds, also referred to herein as cationic steroidal anti-microbial compounds (CSAs), are synthetically produced small molecule chemical compounds that include a sterol backbone having various charged groups (e.g., amine and cationic groups) attached to the backbone. Ceragenins are thought to mimic the structure and function of naturally-occurring anti-microbial peptides and are able to kill and/or sensitize bacteria, fungi, and other microbes.

Ceragenins are able to kill bacteria, fungi, lipid-enveloped viruses, and other microbes by associating with the outer membrane of the microbe and then inserting into the membrane. When inserted into the membrane, ceragenins disrupt the cell's outer membrane and increase ion permeability. Most microbes cannot survive if their membranes are "permeablized" because they, for example, depend on transmembrane ion gradients for ATP production and maintenance of other vital cell functions.

Ceragenins are readily soluble in water and, like most antibiotics, their effectiveness can be diminished or eliminated if they are washed away or diluted. As a result, ceragenins and other antibiotics are generally not very effective for inhibiting microbial growth on surfaces. One technique that has been explored for making antibiotics more active on surfaces (e.g., polymer surfaces) is to covalently attach the antibiotic to the surface. For example, U.S. Pat. No. 7,854,941 to Urban et al. describes a system for covalently attaching antibiotics (e.g., β-lactam antibiotics) to reactive moieties that are themselves covalently attached to a polymer surface. By selecting appropriate antibiotics, growth of both Gram-negative and Gram-positive bacteria on the polymer surface can be inhibited by such a system.

Alternatively, anti-microbial compounds are delivered in a fluid medium and periodically reapplied to a surface to maintain a low microbial count.

SUMMARY

Disclosed herein are particulate ceragenins and methods for making particulate ceragenins having a desired particle size. The particulate ceragenins manufactured according to the present invention have been found to be surprisingly useful in making composite materials and minimizing survival of microbes over extended periods of time. The ability to kill microbes over a period of time is a consequence of the sizes of the particles and/or their distribution.

Importantly, to achieve the desired particle sizes and/or distribution, the particles are fractured in a milling apparatus at or below a particular moisture content. The moisture content of the ceragenins during manufacturing have been found to be important for obtaining particles suitable for use in making composites with desired strength and other mechanical properties.

In one embodiment, the particulate ceragenin materials may be manufactured by: m (i) providing a ceragenin feed material comprised of ceragenin molecules, each having a sterol backbone and a plurality cationic groups attached thereto; (ii) fracturing the ceragenin feed material in a milling apparatus to produce a ceragenin particulate material having a particle size distribution with a median particle size in a range from 5 nm to 20 μm; and (iii) performing the fractioning under conditions where the ceragenin feed has a moisture content of less than or equal to 10% by weight. Preferably the moisture content of the ceragenin materials is less than or equal to 5%, or less than or equal to 1%.

The milling apparatus used in the methods of the invention can be any type of milling apparatus that can comminute ceragenins at a moisture content less than or equal to 10% by weight and that can produce a particle size less than or equal to 20 microns, preferably less than about 15 μm, more preferably less than about 10 μm.

Fracturing ceragenins in a milling apparatus has produced surprising and unexpected results. Specifically, it has been found that ceragenins fractured to ultrafine particle sizes (e.g., 500 nm) in a milling apparatus (e.g., jet mill) can form agglomerated particles of desired size that have sub particles. The sub particles may be very small, such as on the order of 500 nm. This is unexpected since milling apparatuses such as jet mills tend to produce particles greater than about 1 micron at the smallest.

Examples of suitable particle sizes that have been found to give desired properties to composite materials include particles comminuted according to methods disclosed herein to have a particle size in a range from 100 nm to 15 microns, 500 nm to 10 microns, or 1 microns to 5 microns. Where the particles form agglomerates of sub particles, the agglomerated particles may have a median particle size in a range of 1-20 microns or 1-10 microns and sub particles with an average particle size of less than 1 micron, preferably less than 750 nm or 500 nm.

Particles prepared with the foregoing sizes can have surprising and unexpected results when combined with composite materials. Particulate materials incorporated into composites allow surprisingly better polymerization and can yield desired mechanical properties that are not achievable using ceragenin particulates previously known.

For example, one advantage of ceragenin particles of the present invention is their low surface area as compared to dissolved ceragenins. The low surface area allows more ceragenin particles to be incorporated into a composite without creating a viscous solution. In addition, by decreasing the particles size to less than 20 μm, more preferably 15 μm or 10 μm, the pore sizes of composites incorporating the particles have reduced effect on the mechanical properties of the material.

In addition, ceragenin particles smaller than 20 microns have been found to dissolve more slowly in some composite materials despite having a higher surface area. It is believed that these smaller particles create a porosity that limits water accessibility, thereby minimizing dissolution.

DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings, in which.

DETAILED DESCRIPTION

I. Ceragenin Compounds

Ceragenin compounds, also referred to herein as cationic steroidal anti-microbial compounds (CSAs), are synthetically produced small molecule chemical compounds that include a sterol backbone having various charged groups (e.g., amine and cationic groups) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I

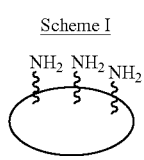

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the cellular membrane of bacteria and other microbes and inserting into the cell membrane forming a pore that allows the leakage of ions and cytoplasmic materials that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the membrane of the bacteria.

The charged groups are responsible for disrupting the bacterial cellular membrane, and without the charged groups, the ceragenin compound cannot disrupt the membrane to cause cell death or sensitization. Examples of ceragenin compounds are shown below as Formula (I) and Formula (II), which are closely related but not identical. As will be discussed in greater detail below, the R groups of Formula (I) and Formula (II) can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring).

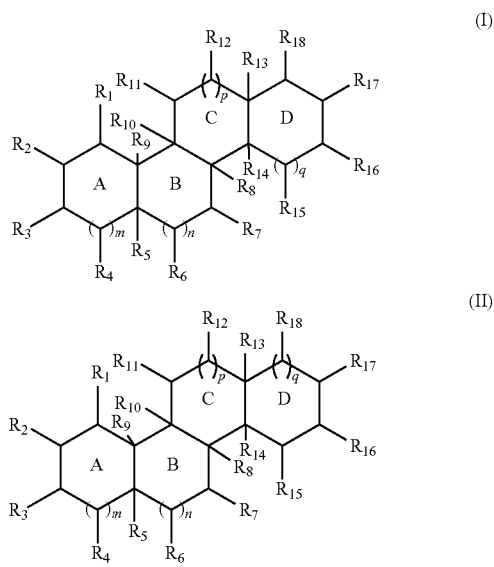

Figure 1A:
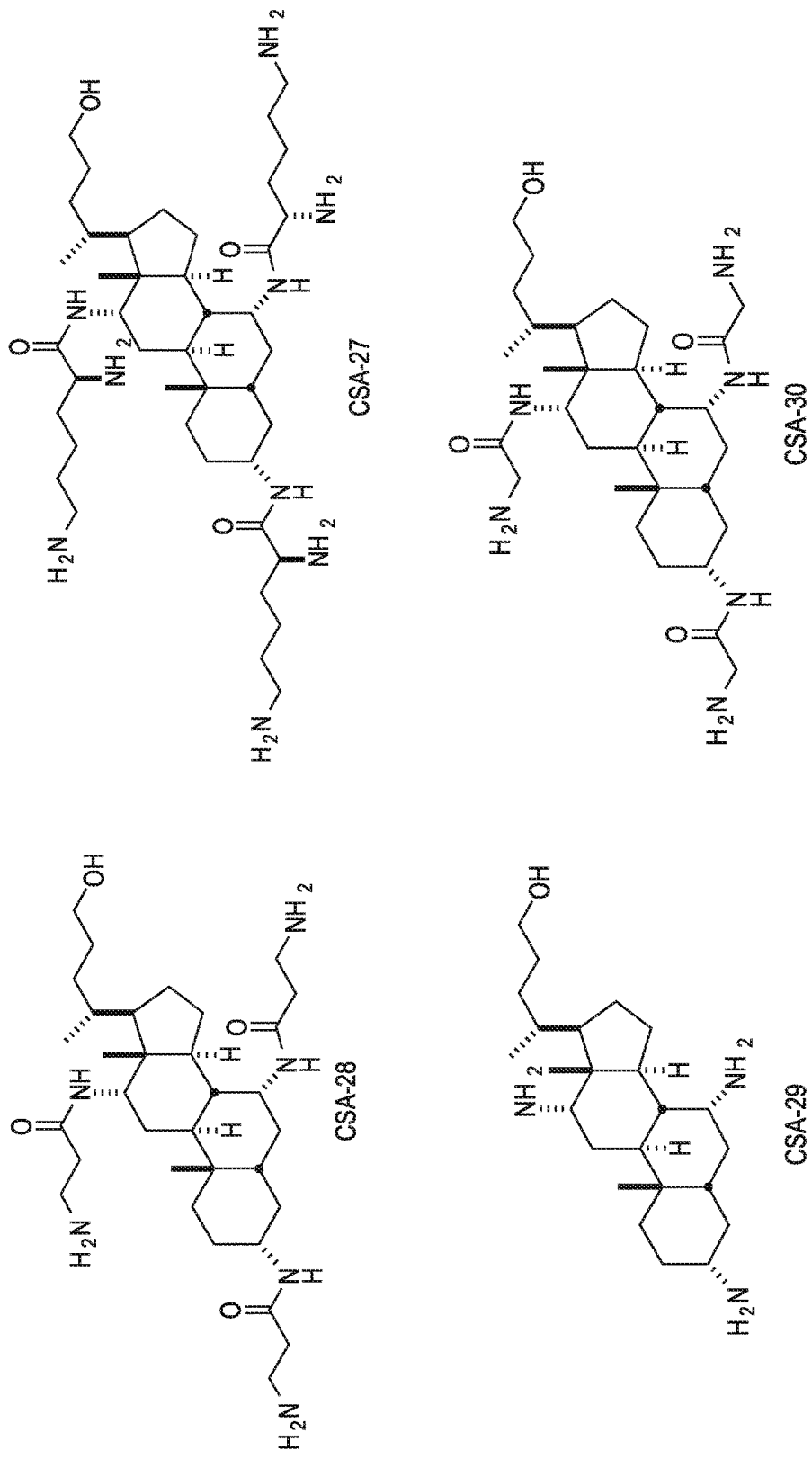
FIG. 1A illustrates exemplary hydrolysable cationic steroidal anti-microbial ("CSA") compounds.
Figure 1A:
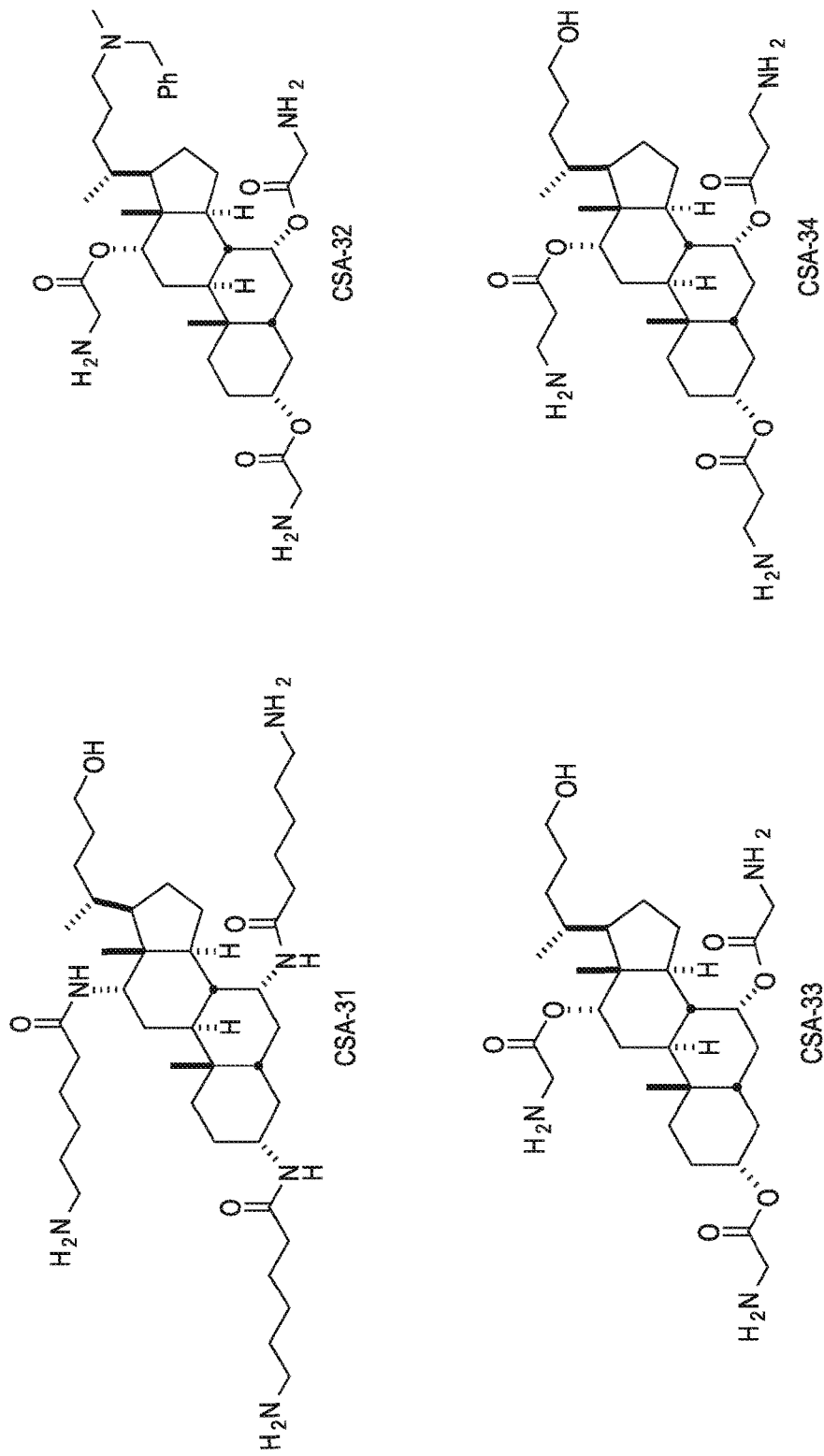
Figure 1A:
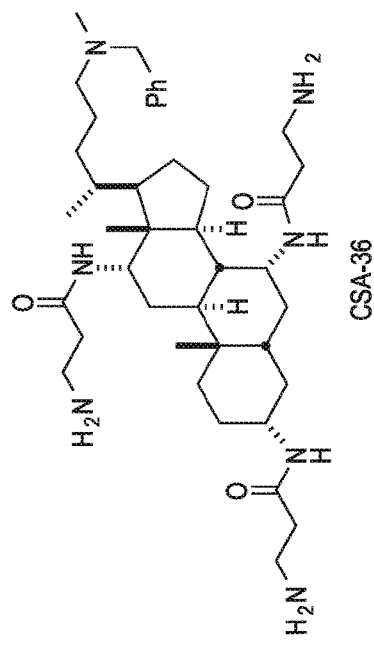
Figure 1A:
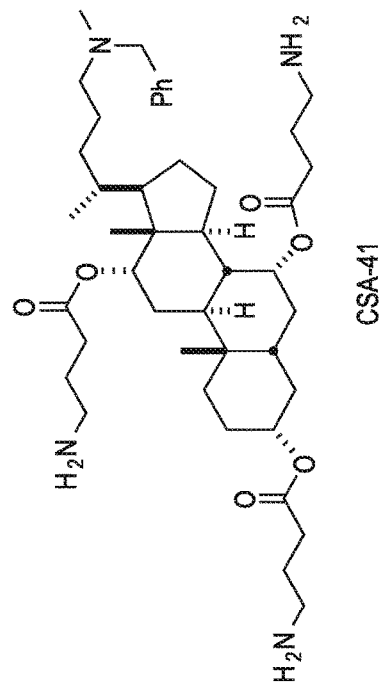
Figure 1A:
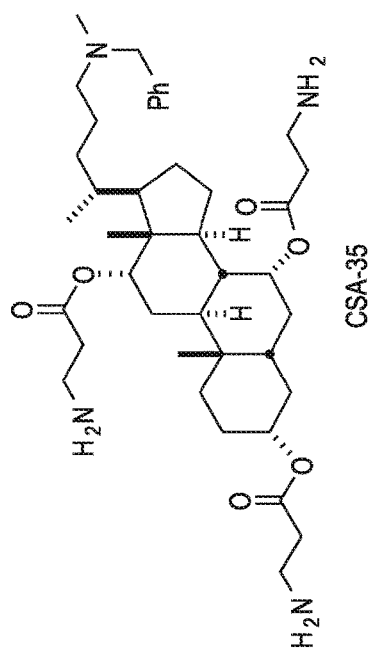
Figure 1A:
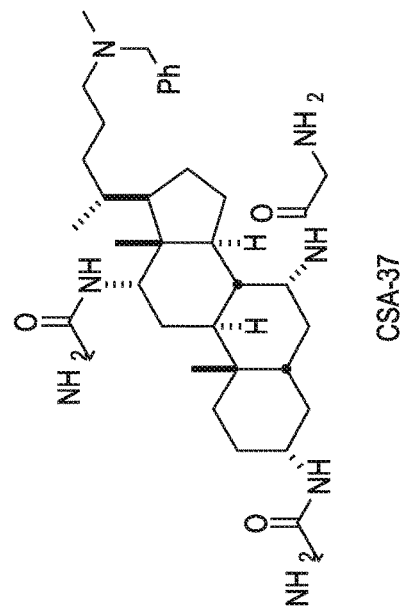
Figure 1A:
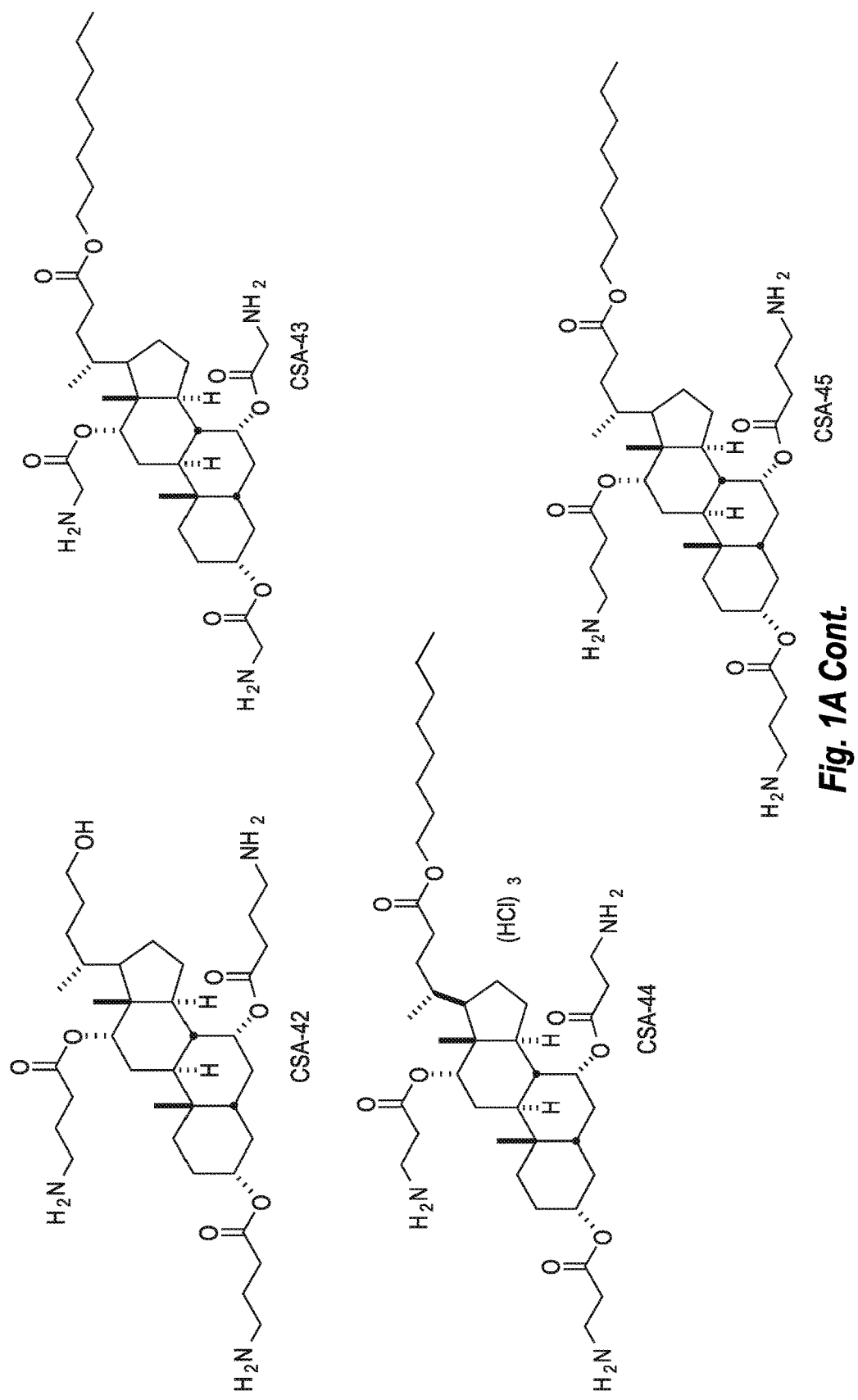
Figure 1A:
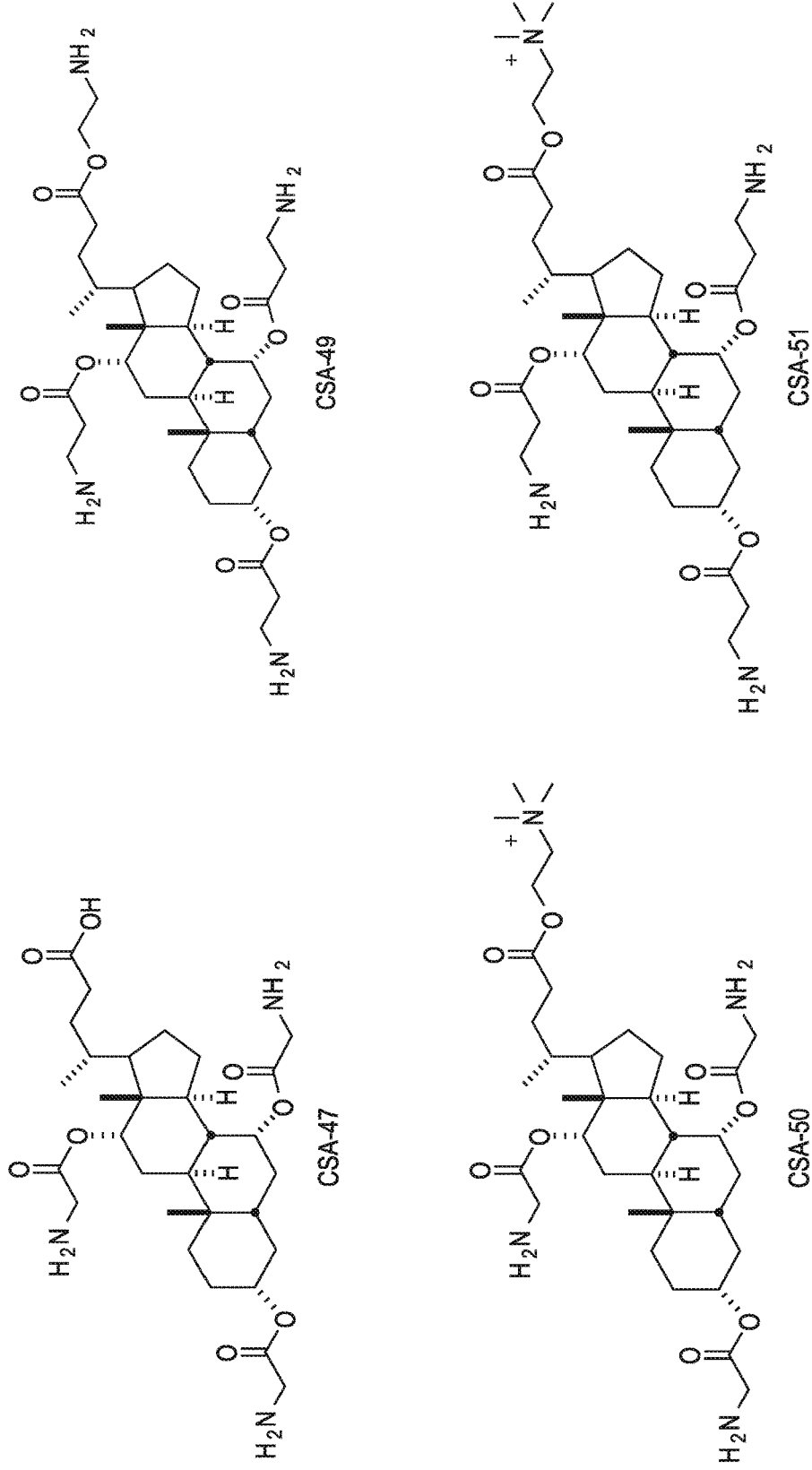
Figure 1A:
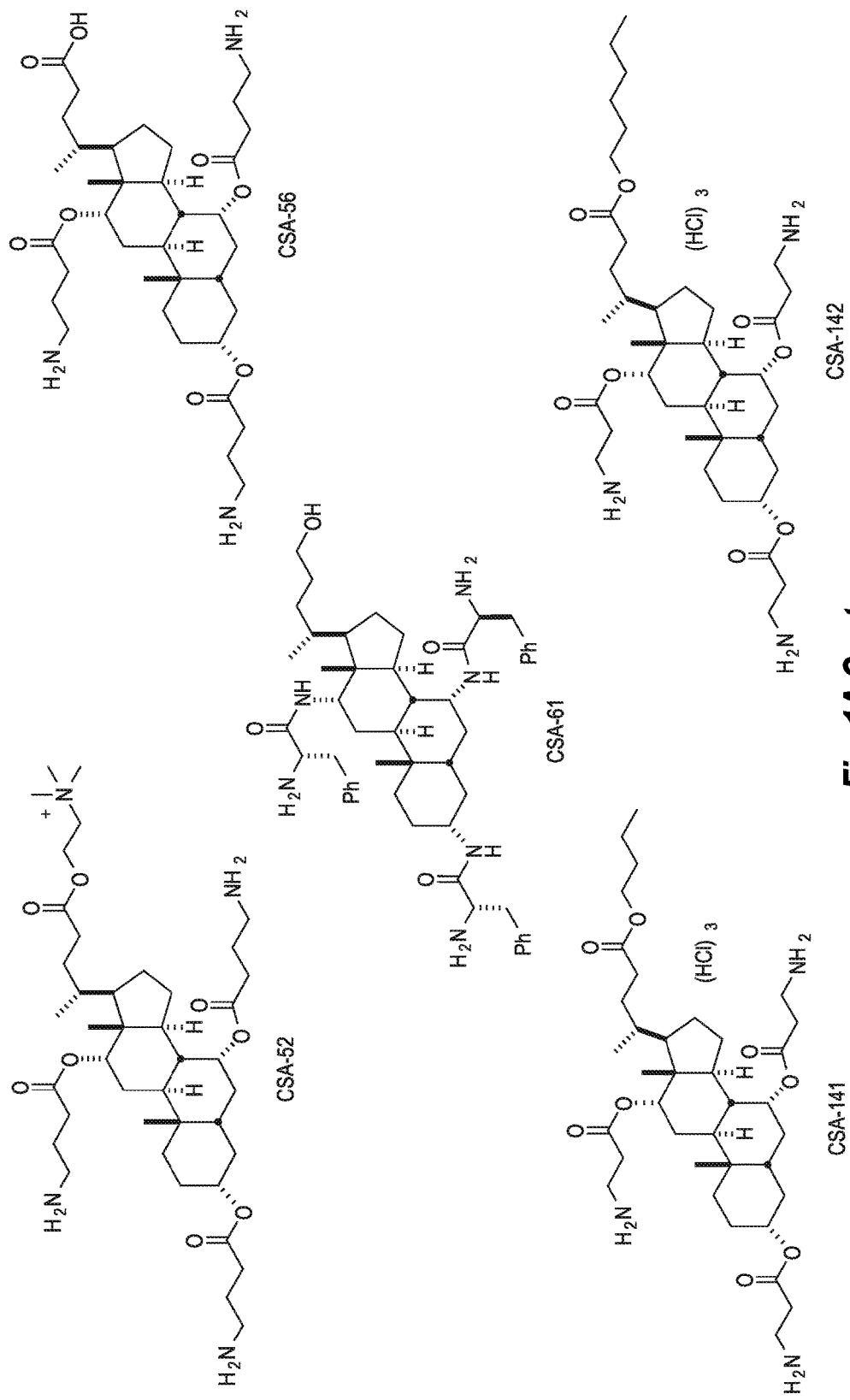
Figure 1B:
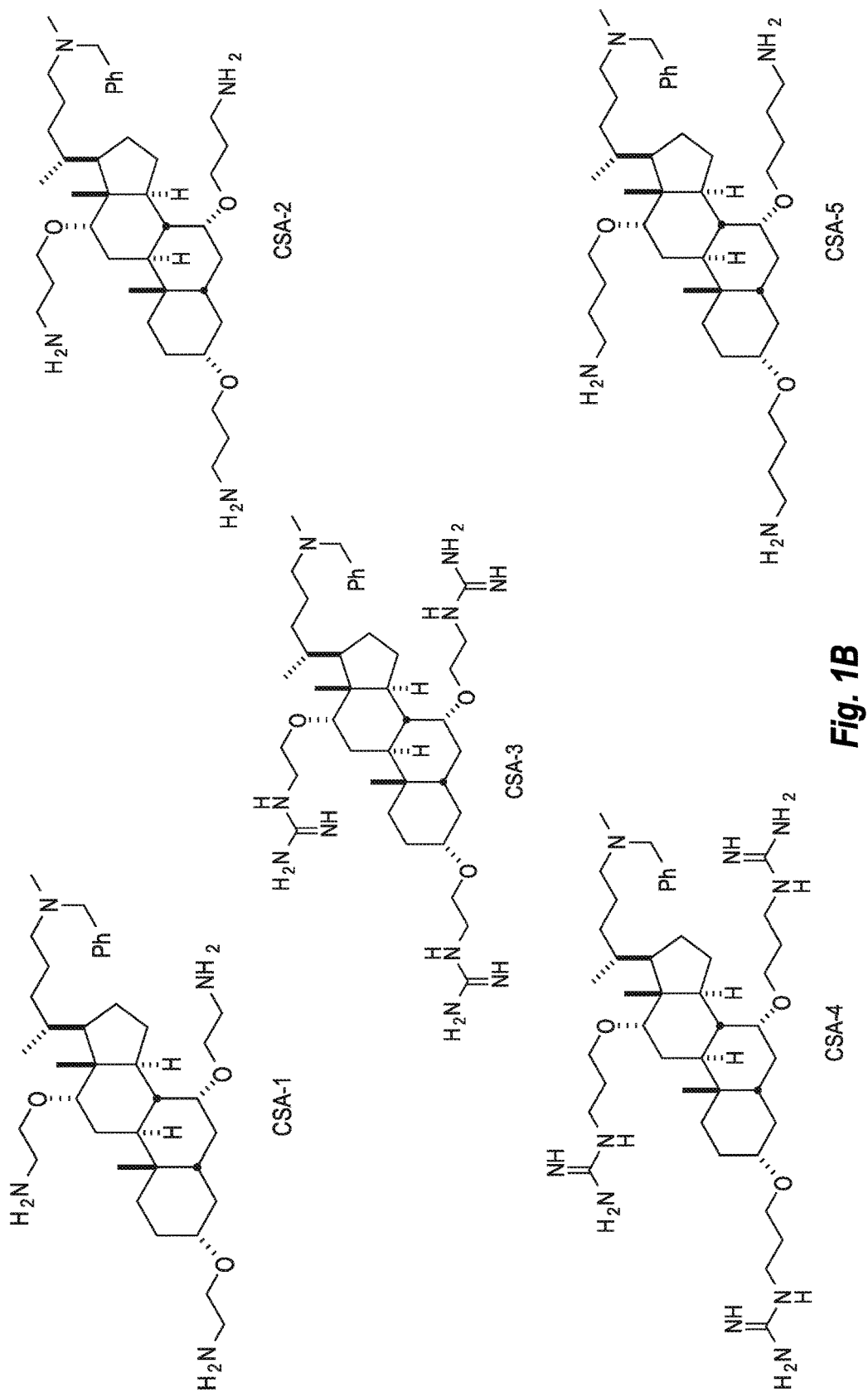
FIG. 1B illustrates exemplary non-hydrolysable CSA compounds.
Figure 1B:
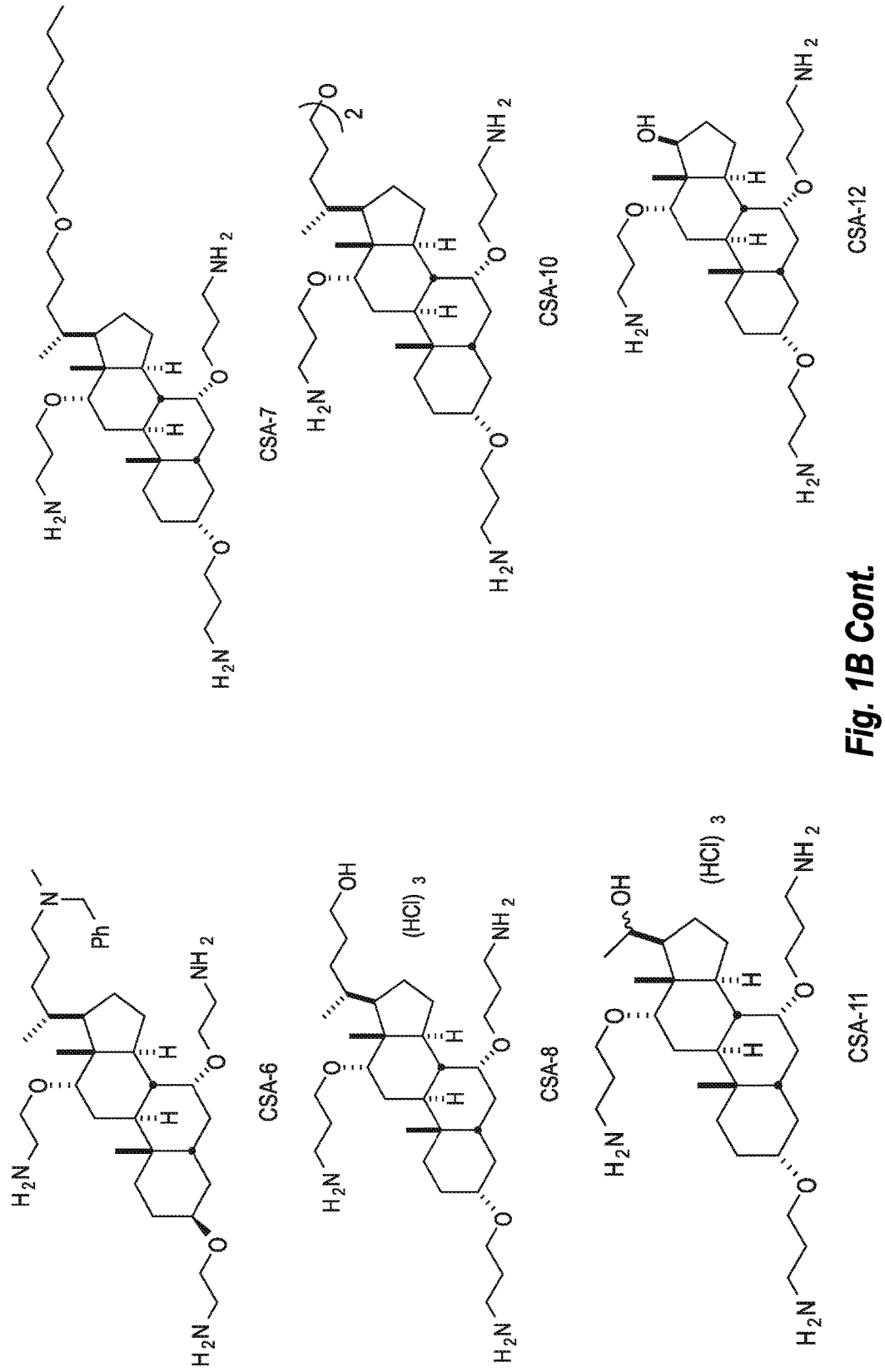
Figure 1B:
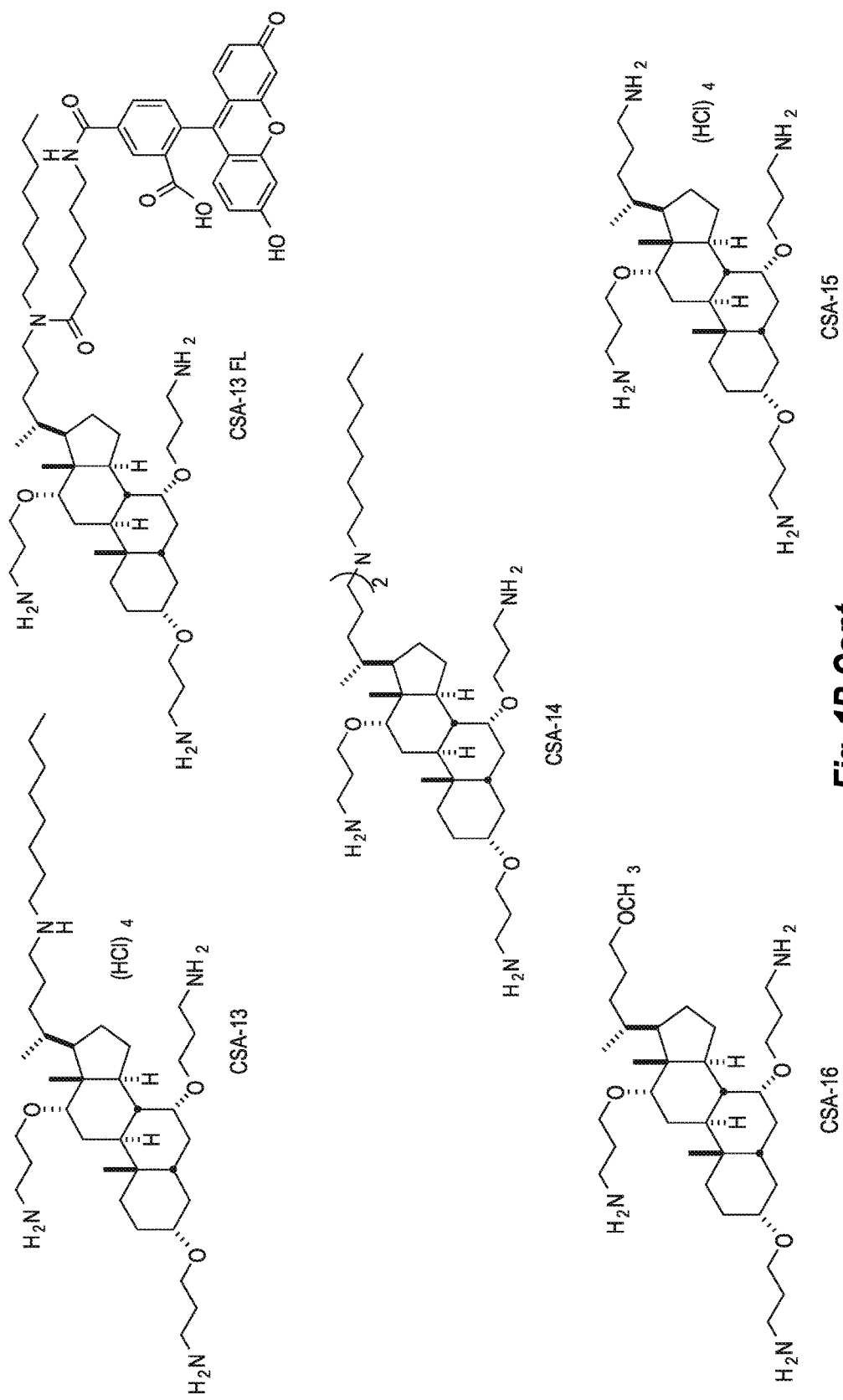
Figure 1B:
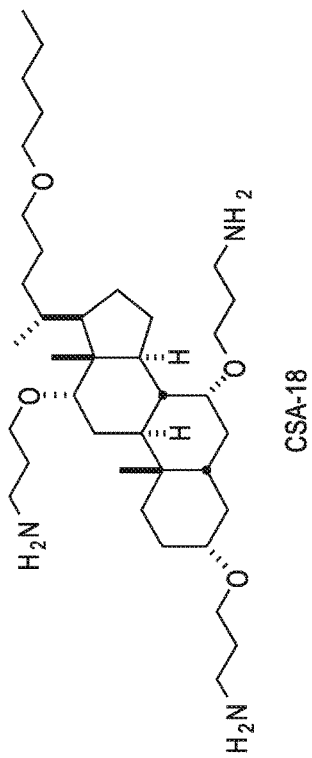
Figure 1B:
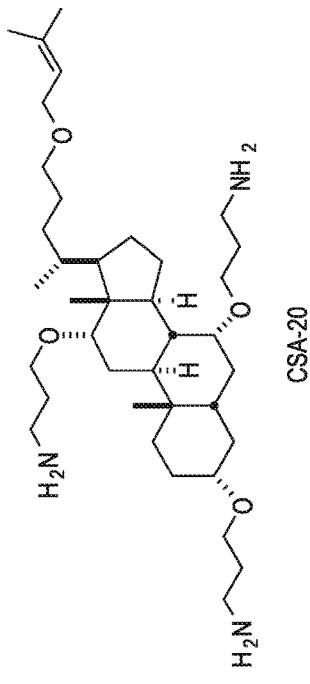
Figure 1B:
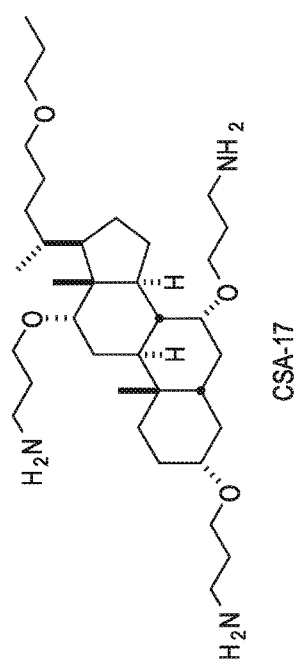
Figure 1B:
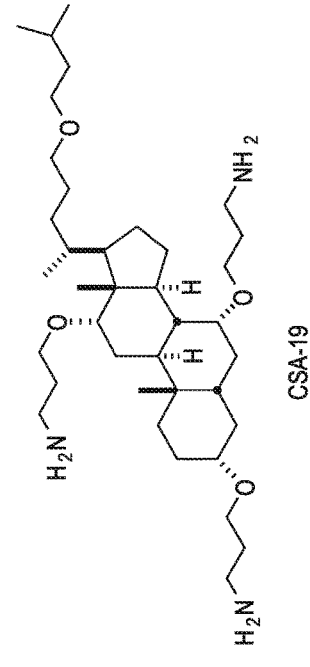
Figure 1B:
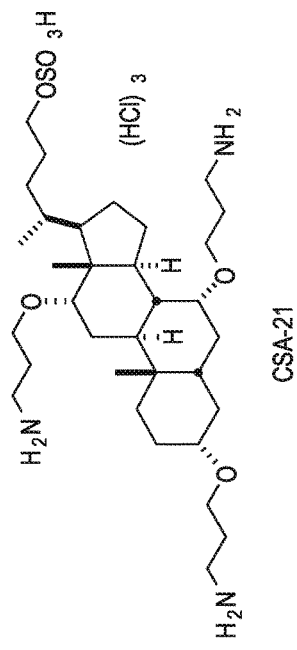
Figure 1B:
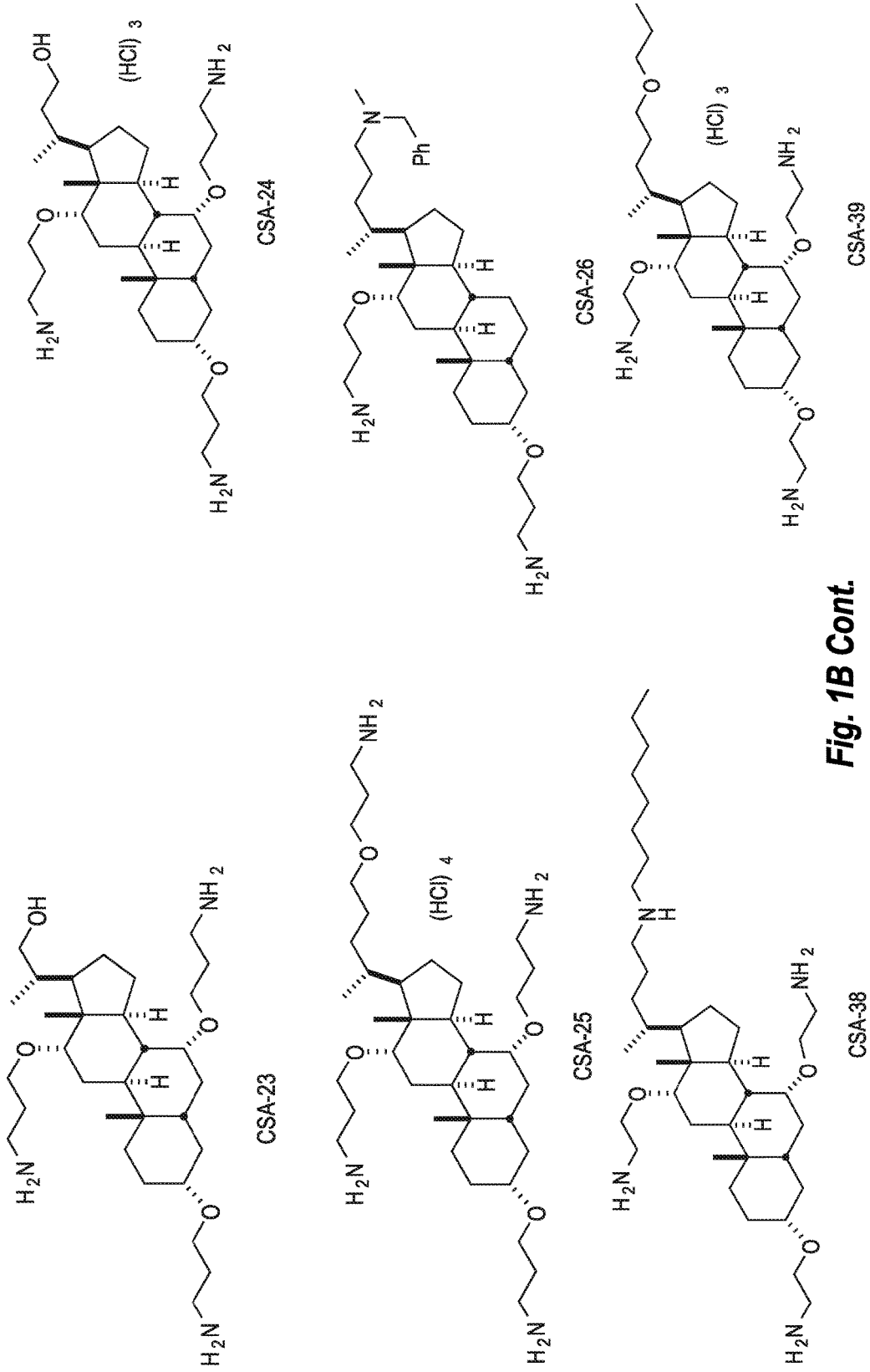
Figure 1B:
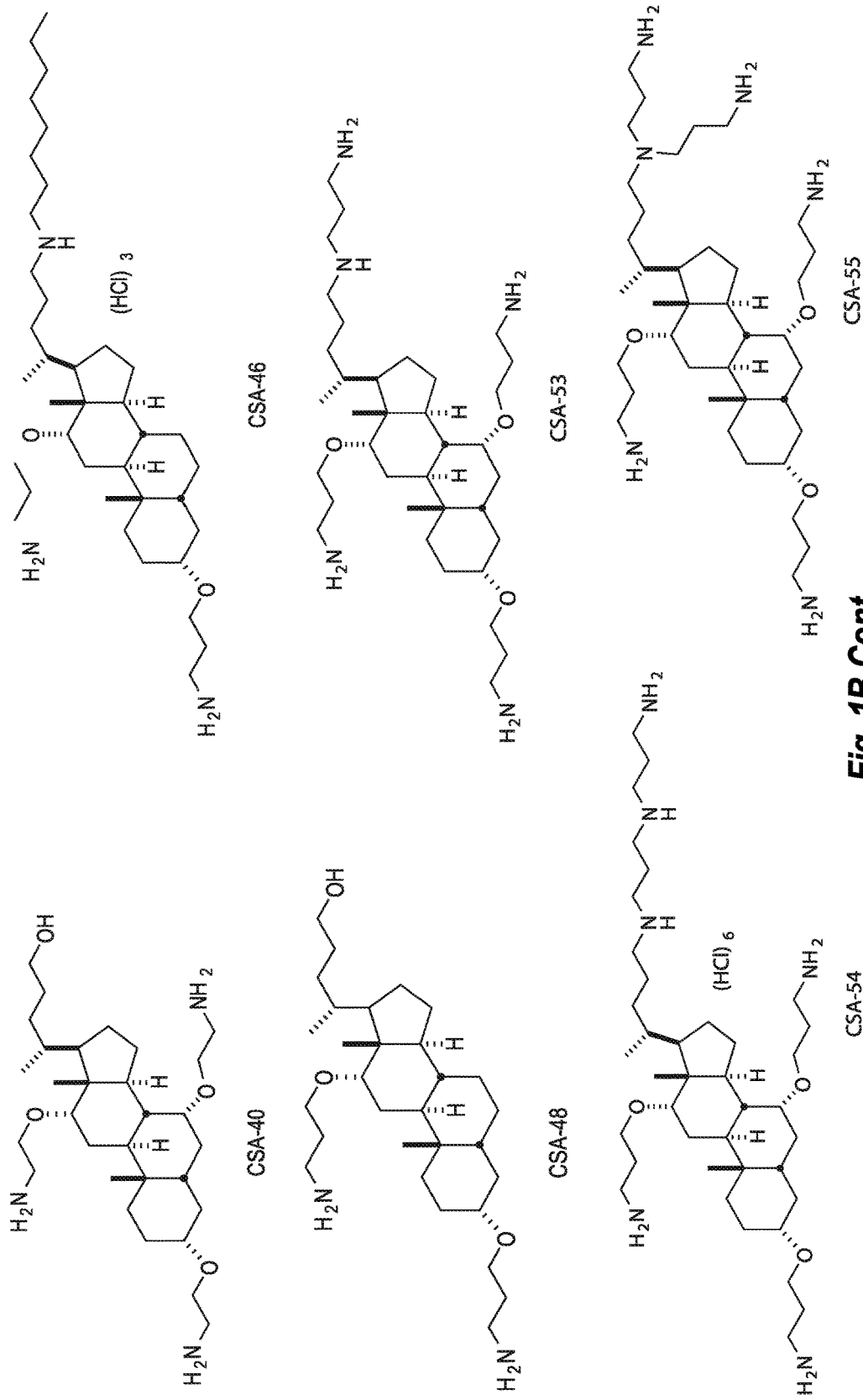
Figure 1B:
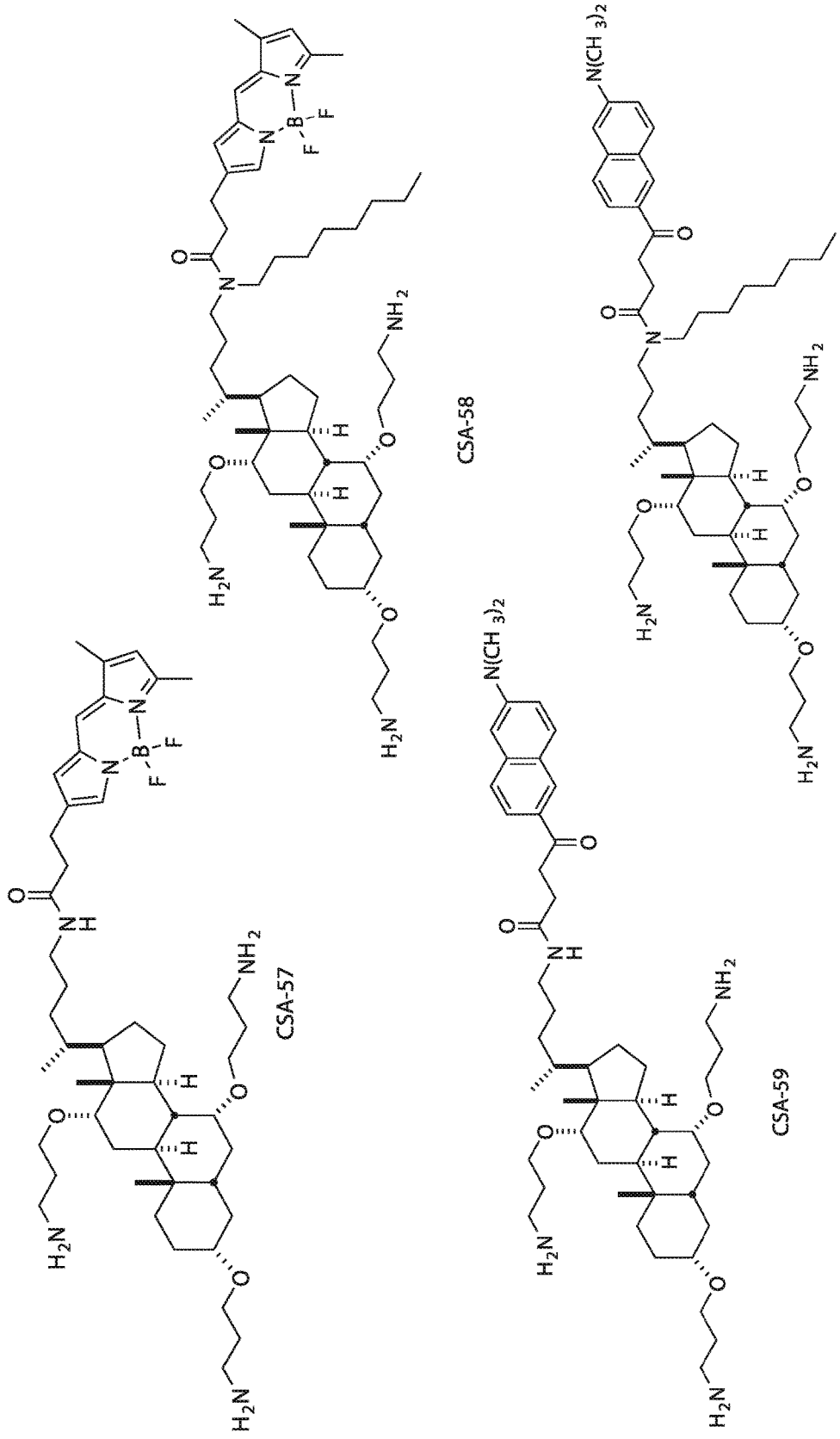
Figure 1B:
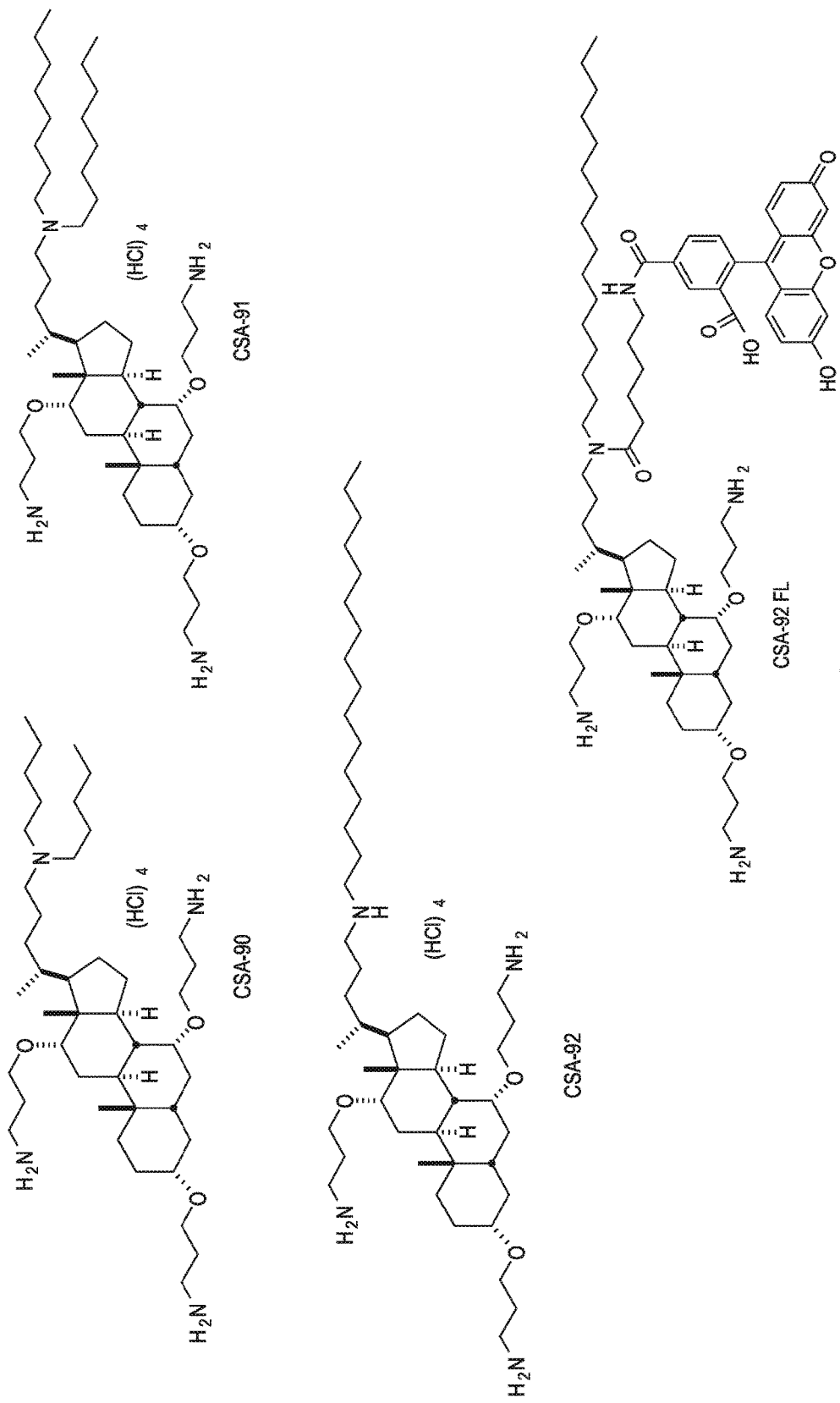
Figure 1B:
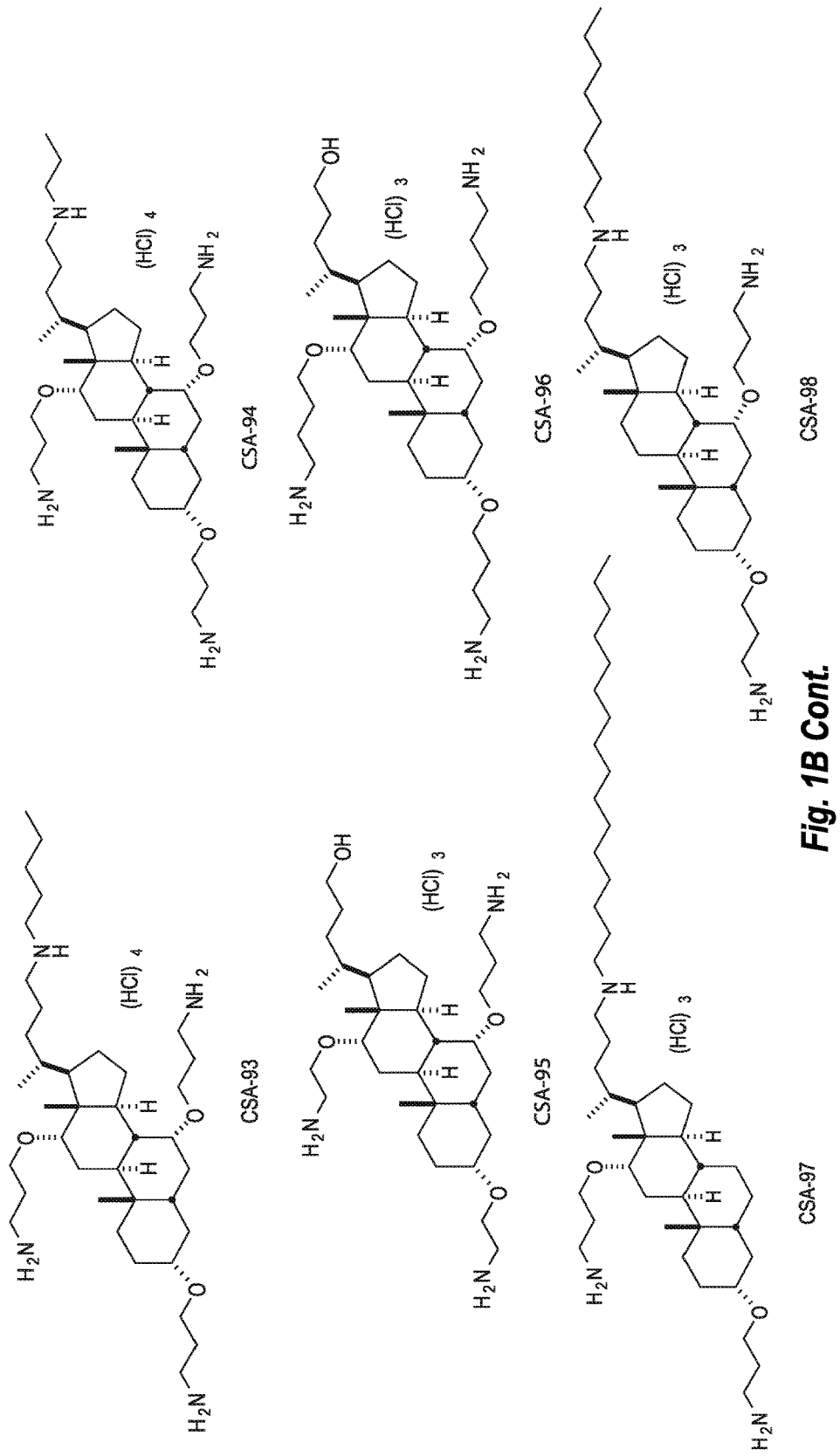
Figure 1B:
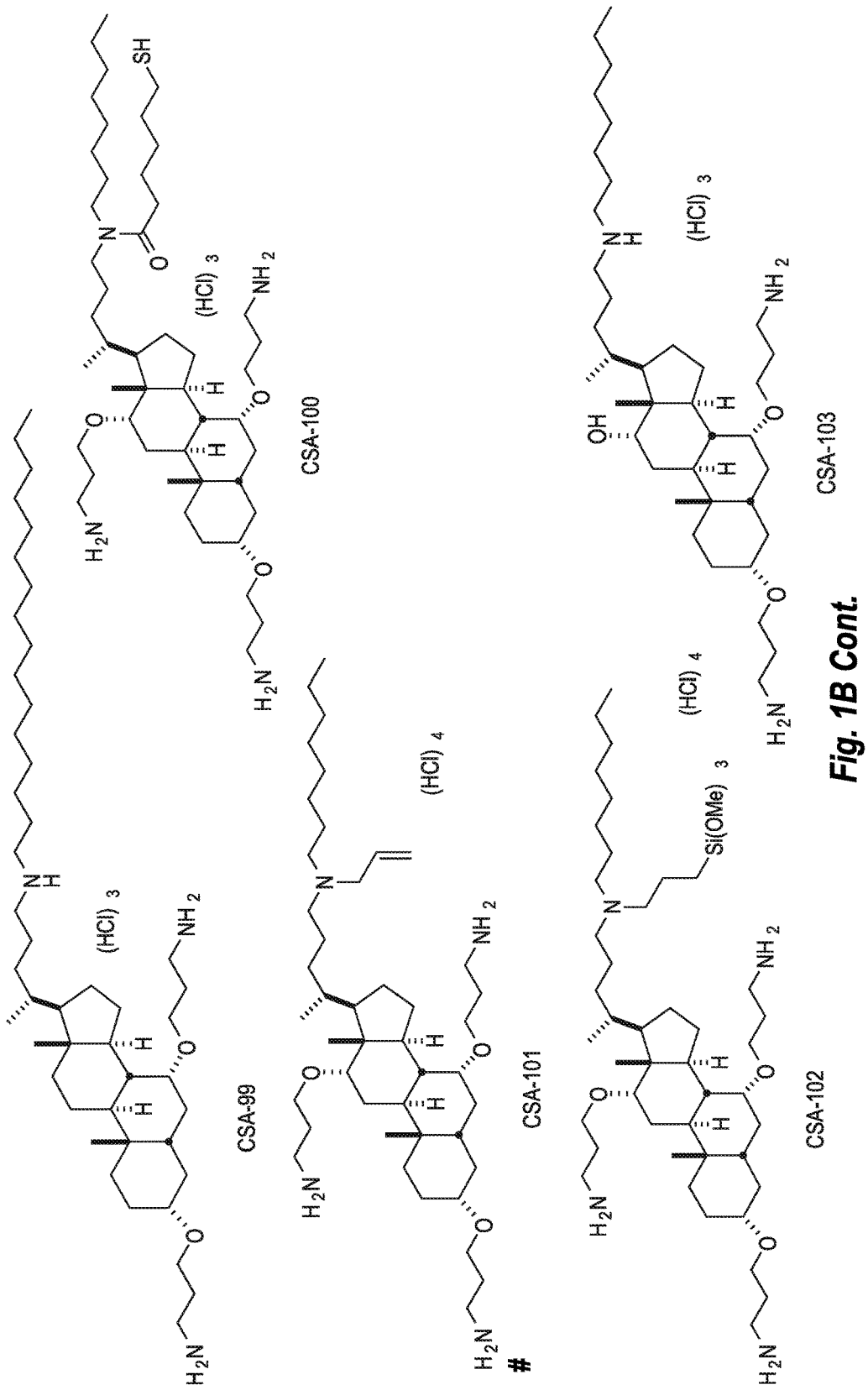
Figure 1B:
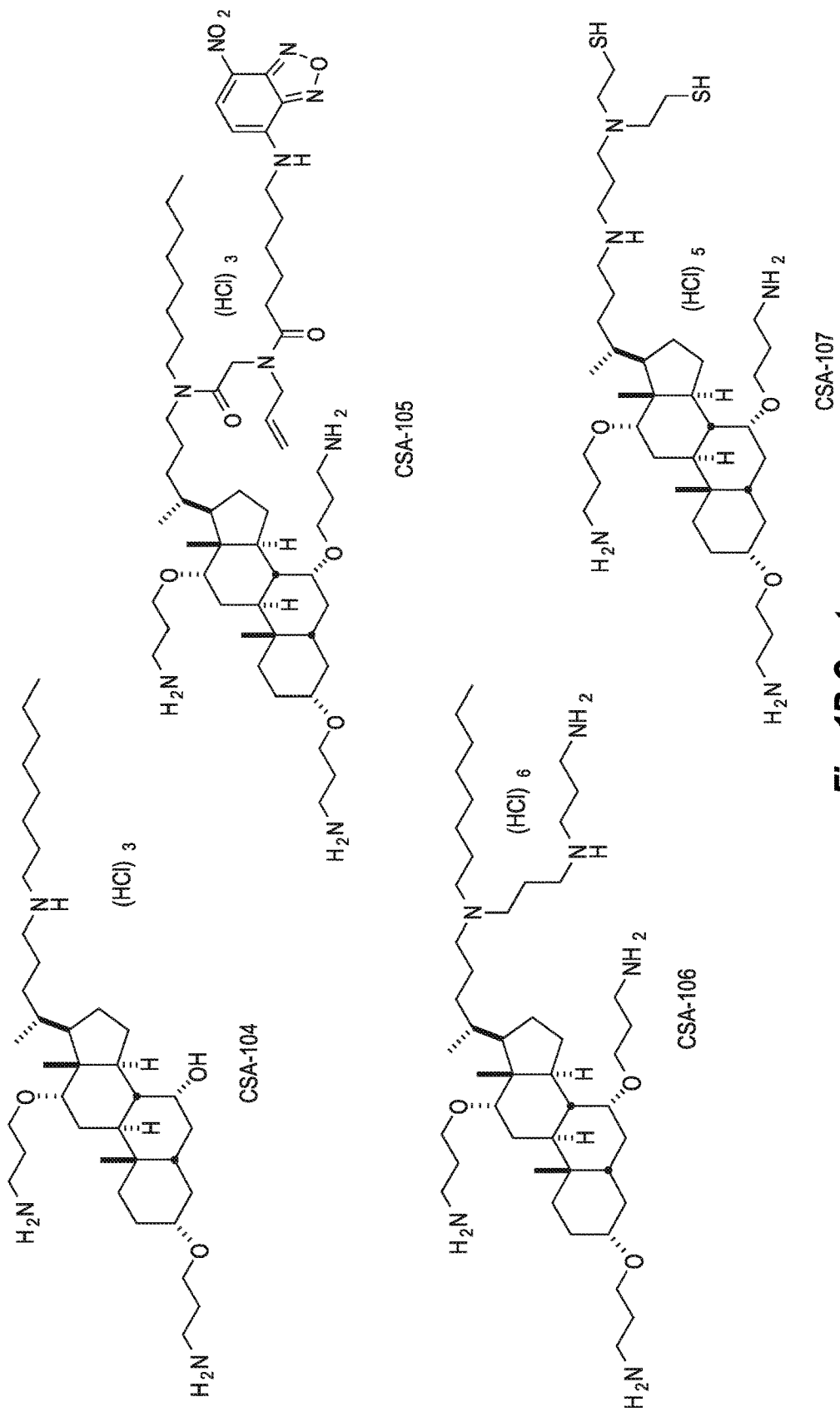
Figure 1B:
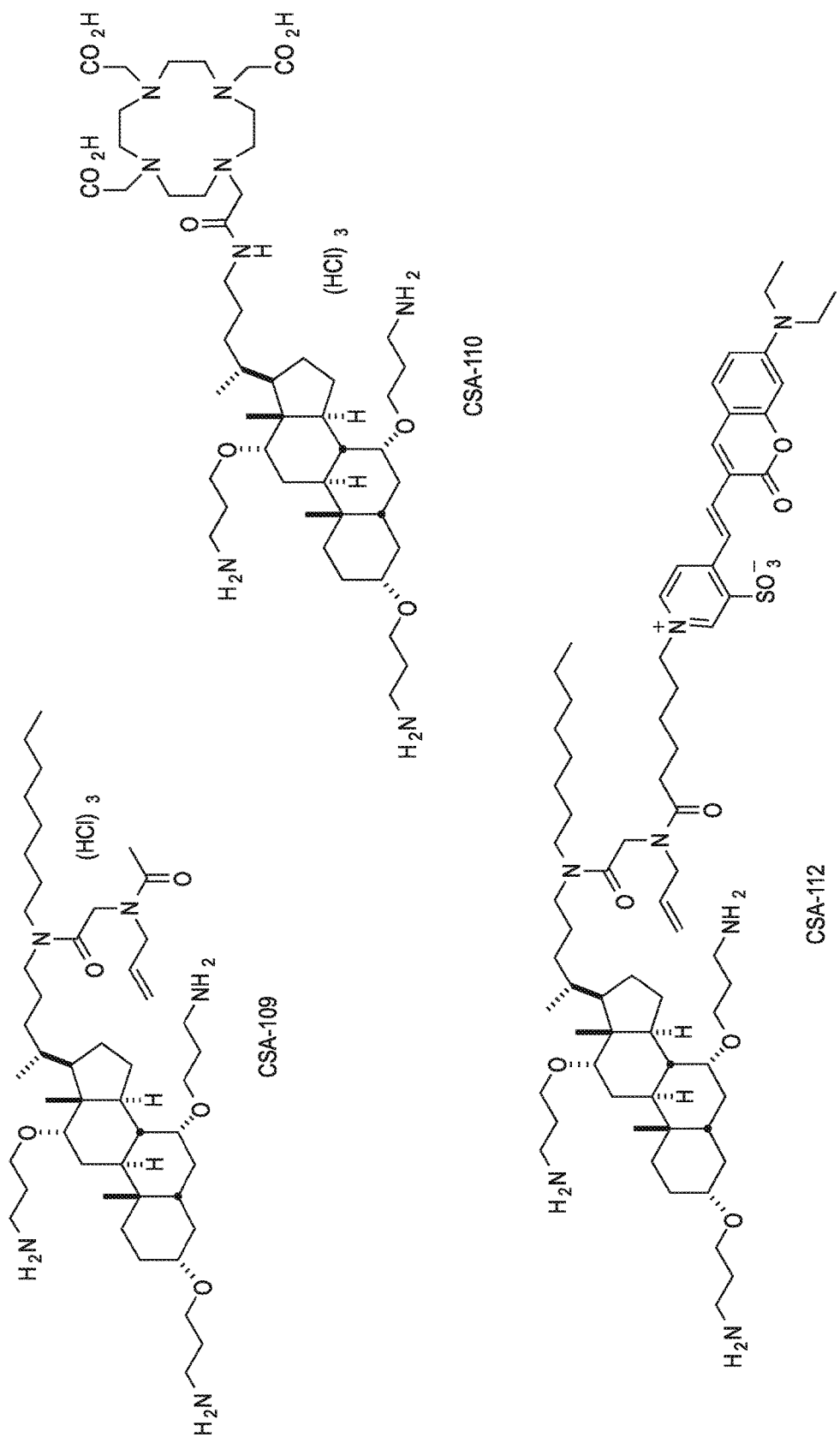
Figure 1B:
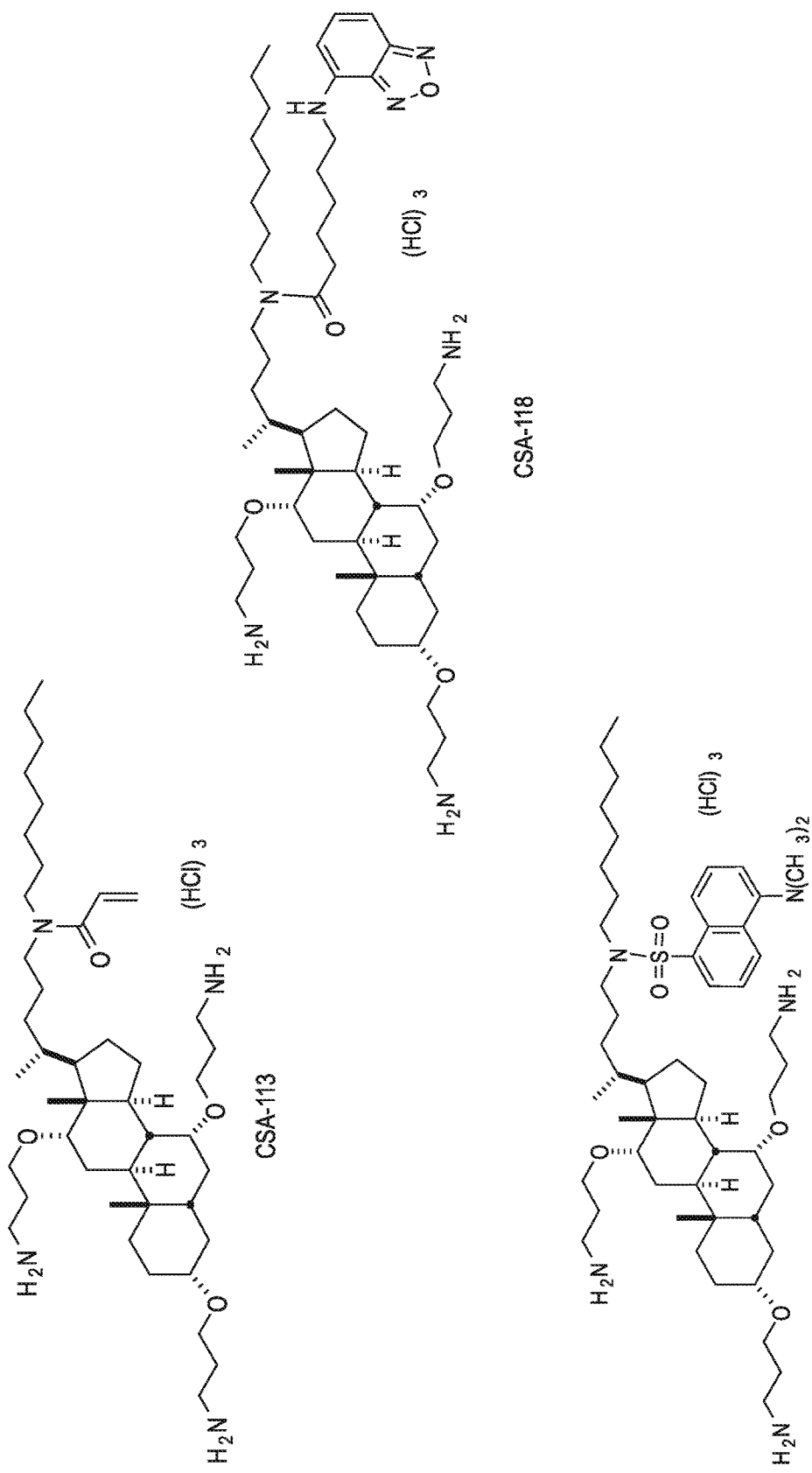
Figure 1B:
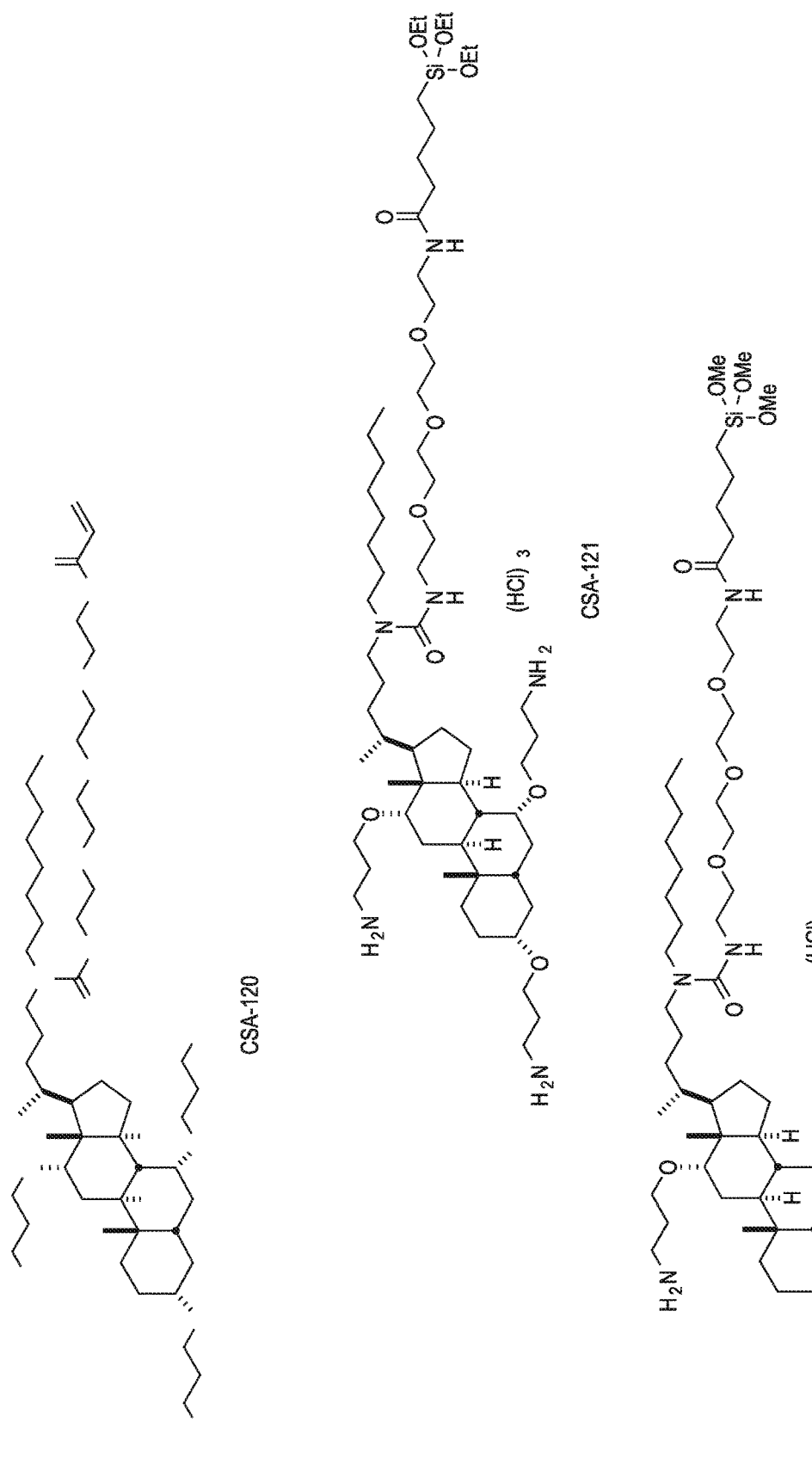
Figure 1B:
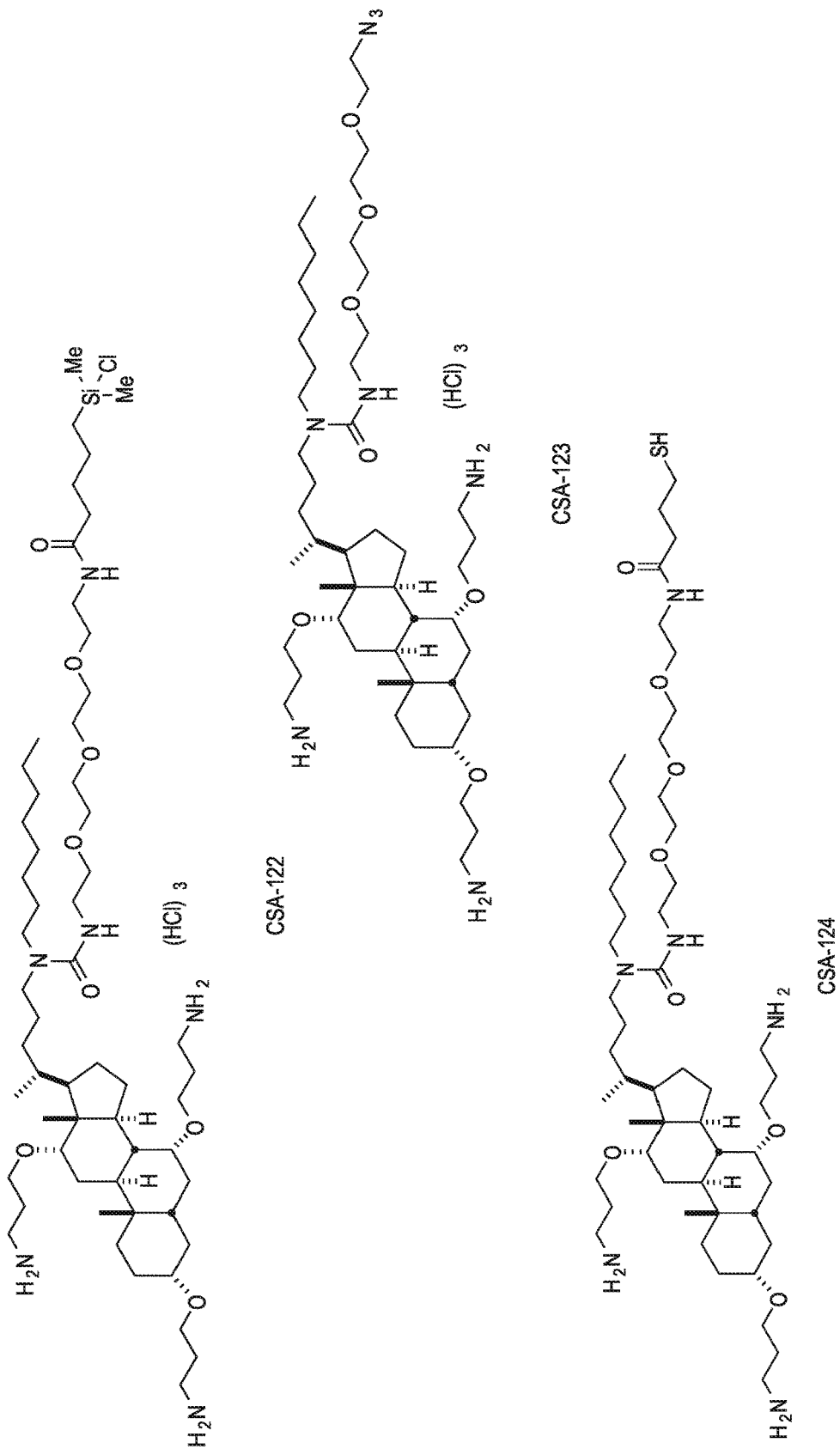
Figure 1B:
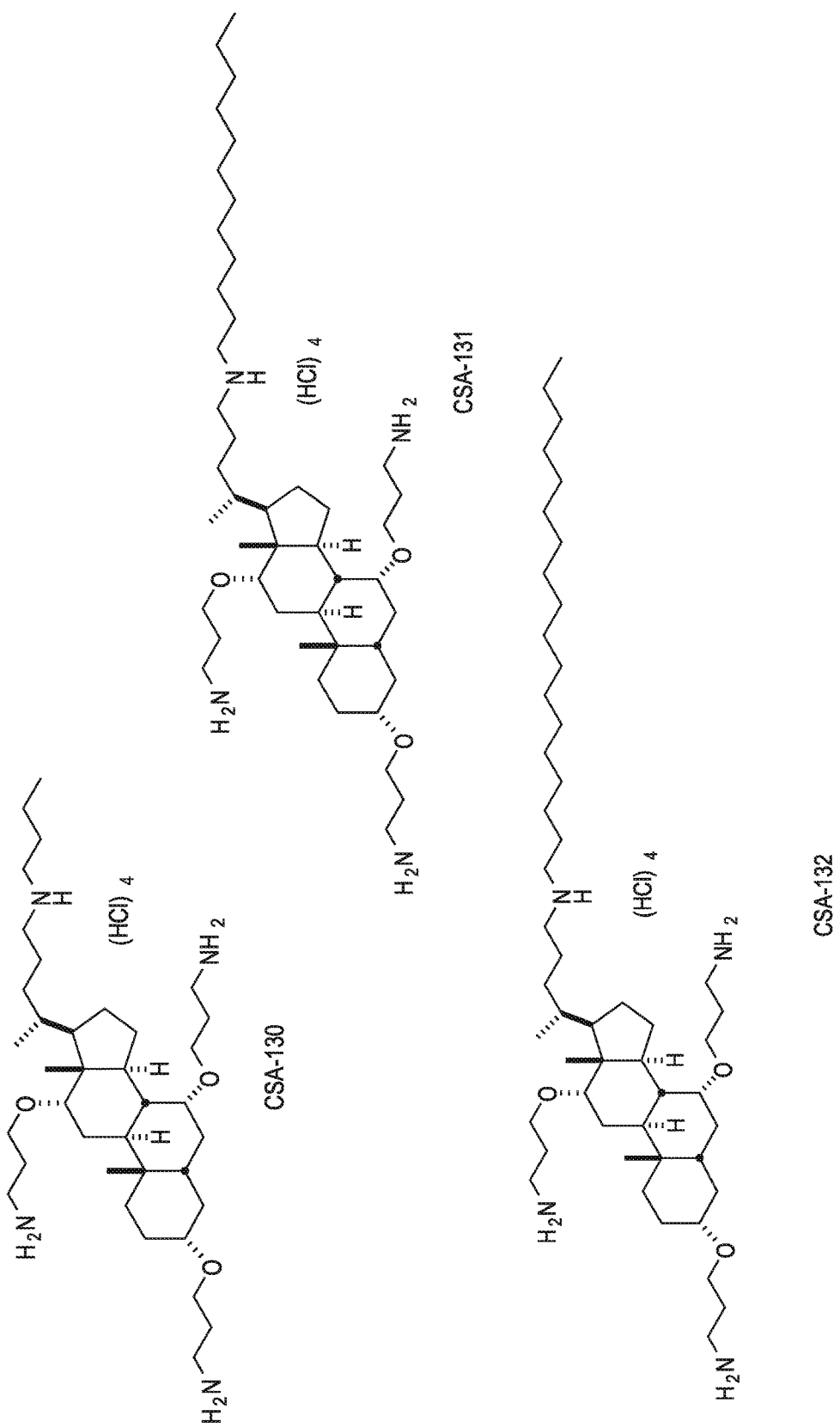
Figure 1B:
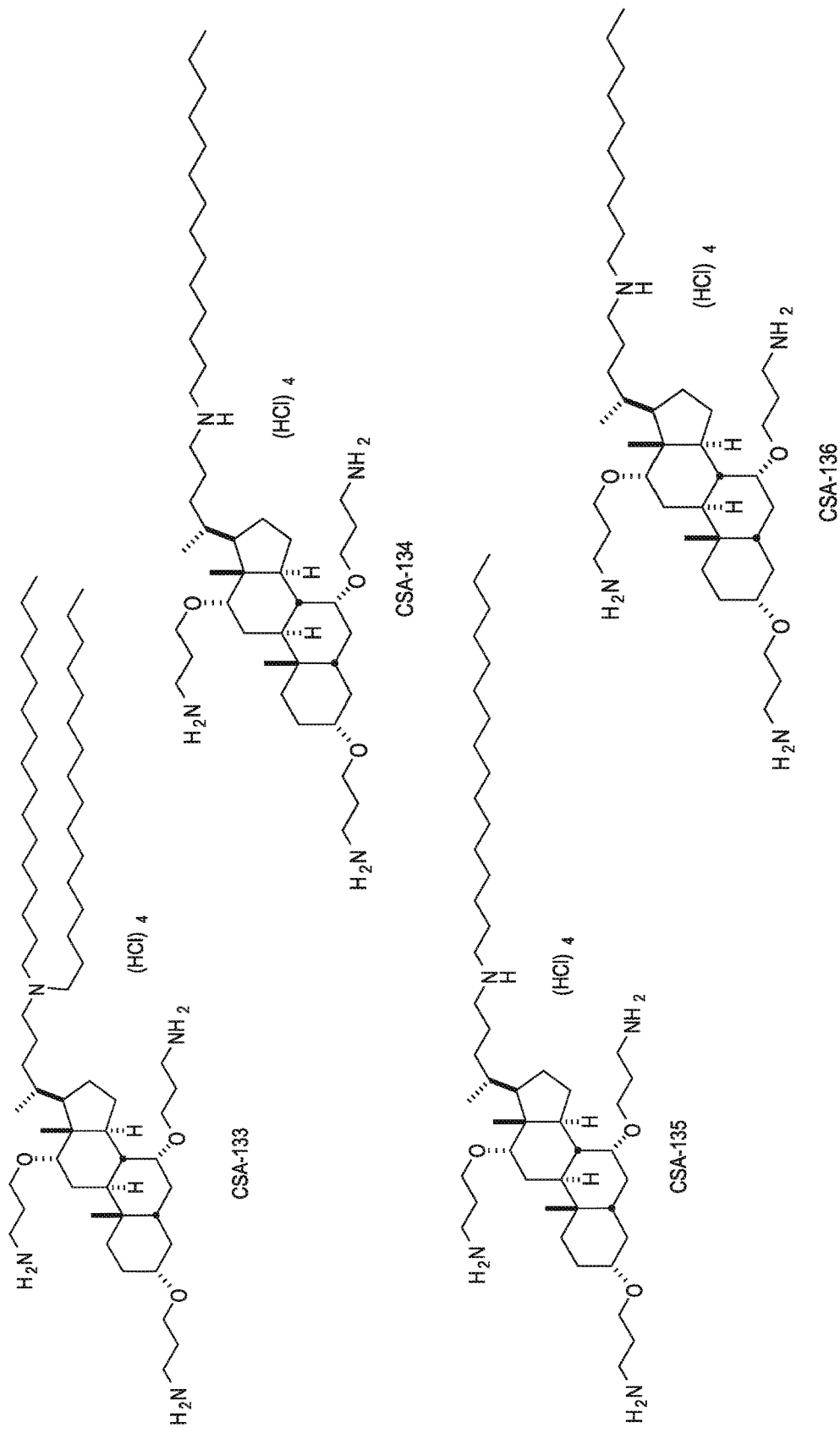
Figure 1B:
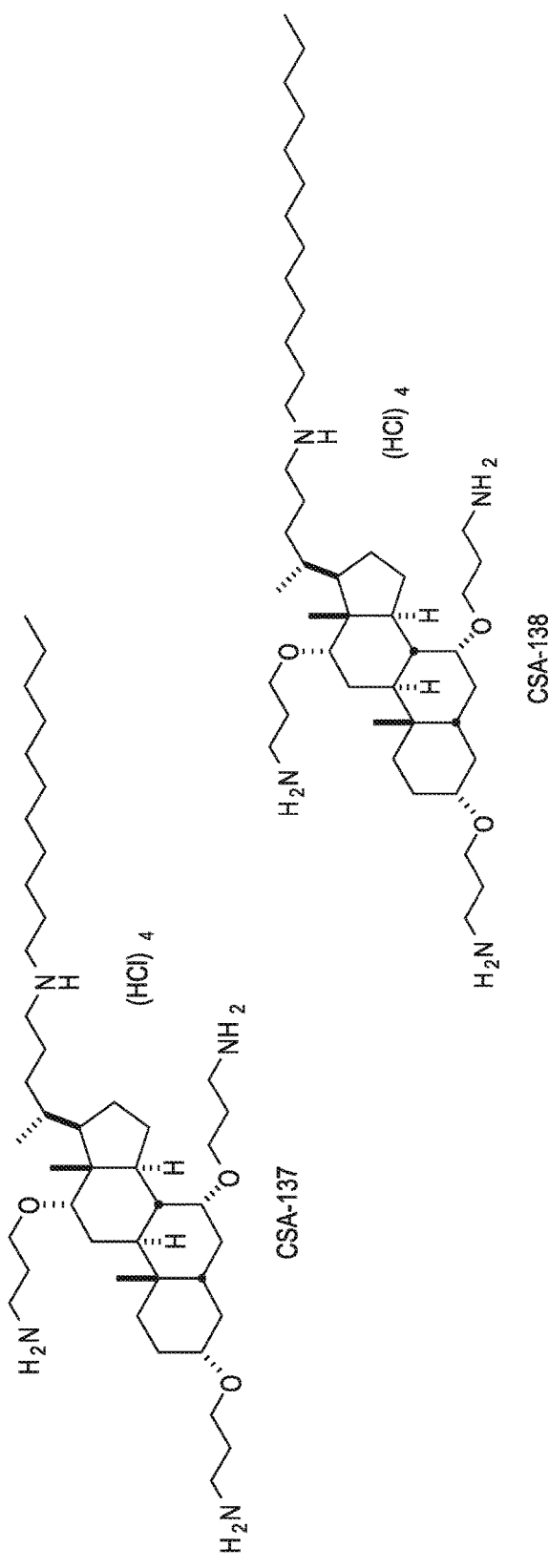
Figure 1B:
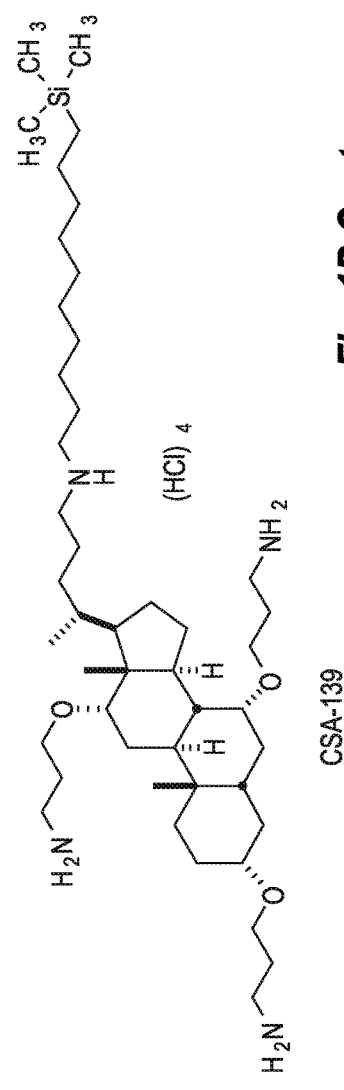

Examples of ceragenin compounds that can be used herein are illustrated in FIGS. 1A and 1B. Typically, ceragenins of Formula (I) and Formula (II) are of two types: (1) ceragenins having cationic groups linked to the sterol backbone with hydrolysable linkages and (2) ceragenins having cationic groups linked to the sterol backbone with non-hydrolysable linkages. FIG. 1A shows examples of hydrolysable cationic steroidal anti-microbial ("CSA") compounds. FIG. 1B shows examples of non-hydrolysable CSA compounds.

Ceragenins of the first type can be "inactivated" by hydrolysis of the linkages coupling the cationic groups to the sterol backbone. For example, one type of hydrolysable linkage is an ester linkage. Esters are hydrolysed in the presence of water and base. Ceragenins of the first type are desirable, for example, where it is preferred that the ceragenins break down so that they do not buildup in the environment. Ceragenins of the second type are not readily inactivated by hydrolysis. They are desired where long-term stability in an aqueous environment is preferred. Ceragenins of the second type are preferred where long-term activity or long-term storage are needed. Ceragenins of either type can be employed in the aerosols described herein.

II. Feed Materials

Feed materials used in the present invention includes at least one type of ceragenin molecules alone or in combination with grinding aids, desiccants, excipients or other materials that require intimate mixing with the ceragenins or that are useful for achieving the desired particle size and/or moisture content.

The feed material may be a powdered material with a particle size substantially larger than the desired particle size of the ceragenin material after milling. The feed material may have a particle size greater than 20 microns, 50 microns, 100 microns, or even 200 microns and/or less than 0.5 mm, 200 microns, 100 microns, or 50 microns or within a range defined by any of the foregoing upper and lower sizes.

The feed material may be a dried ceragenin that is unground or it may be pre-ground using any known grinding methods and at any moisture content to achieve the desired particle size for use as a feed material in the milling apparatus that will produce the desired particle size and morphology suitable for use in composite materials.

The feed material is provided or dried to have a moisture content that will allow particles of a desired size and morphology to be formed in the milling apparatus. The moisture content is less than or equal to 10% and is preferably much less. The moisture content may be less than 5% or 1% or less. These moisture contents have been found to be critical to achieving the desired particle sizes and morphology (e.g., particles less than 5 microns) in instances where no grinding aid or desiccant is used.

The feed material may include grinding aids for achieving the desired particle sizes, distributions, morphology, and/or other properties of the finished product.

Excipients are compounds that act as a carrier or for the ceragenin compounds. Examples of excipients include starches, sugars, cellulose, and magnesium stearate. The excipient may be citrate or lactate.

The present invention may also include desiccants to provide and/or maintain a desired moisture content during fraction of the ceragenins in the milling apparatus. Examples of desiccants include calcium sulfate, calcium chloride, and silica gel.

III. Milling Apparatuses

Figure 2:
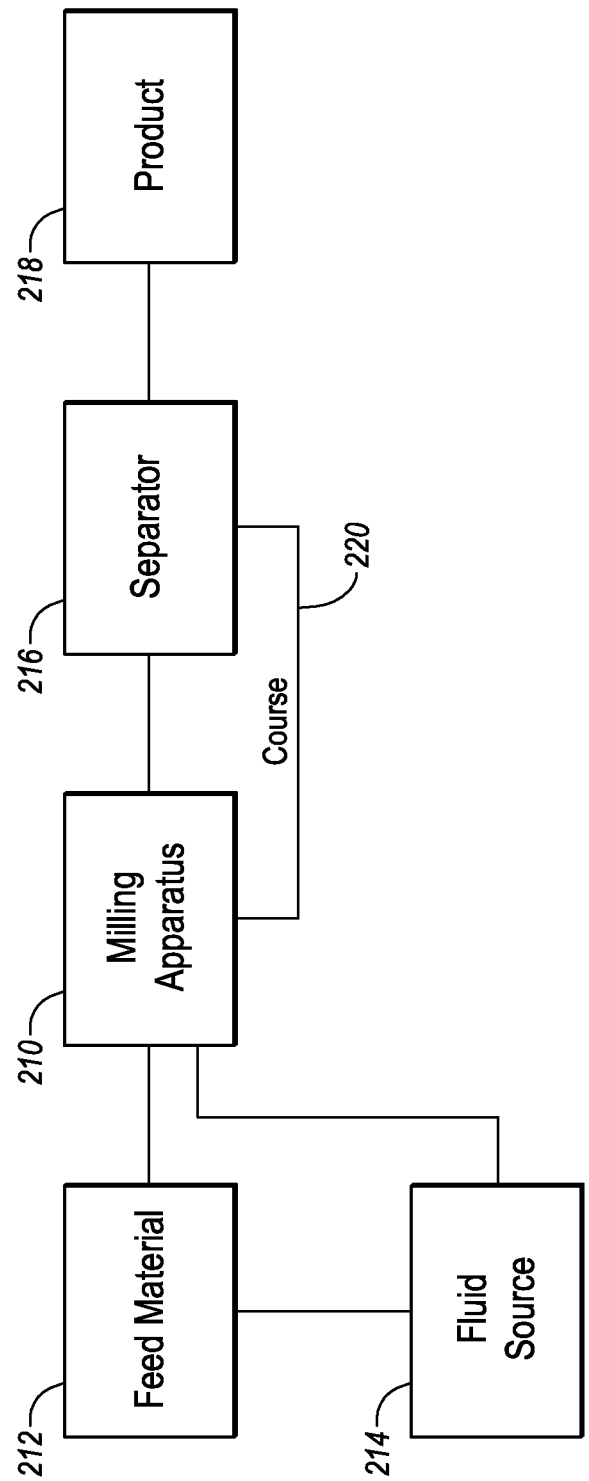
FIG. 2 illustrates a milling circuit suitable for comminuting ceragenin compounds according to one embodiment of the present invention.
Figure 3:
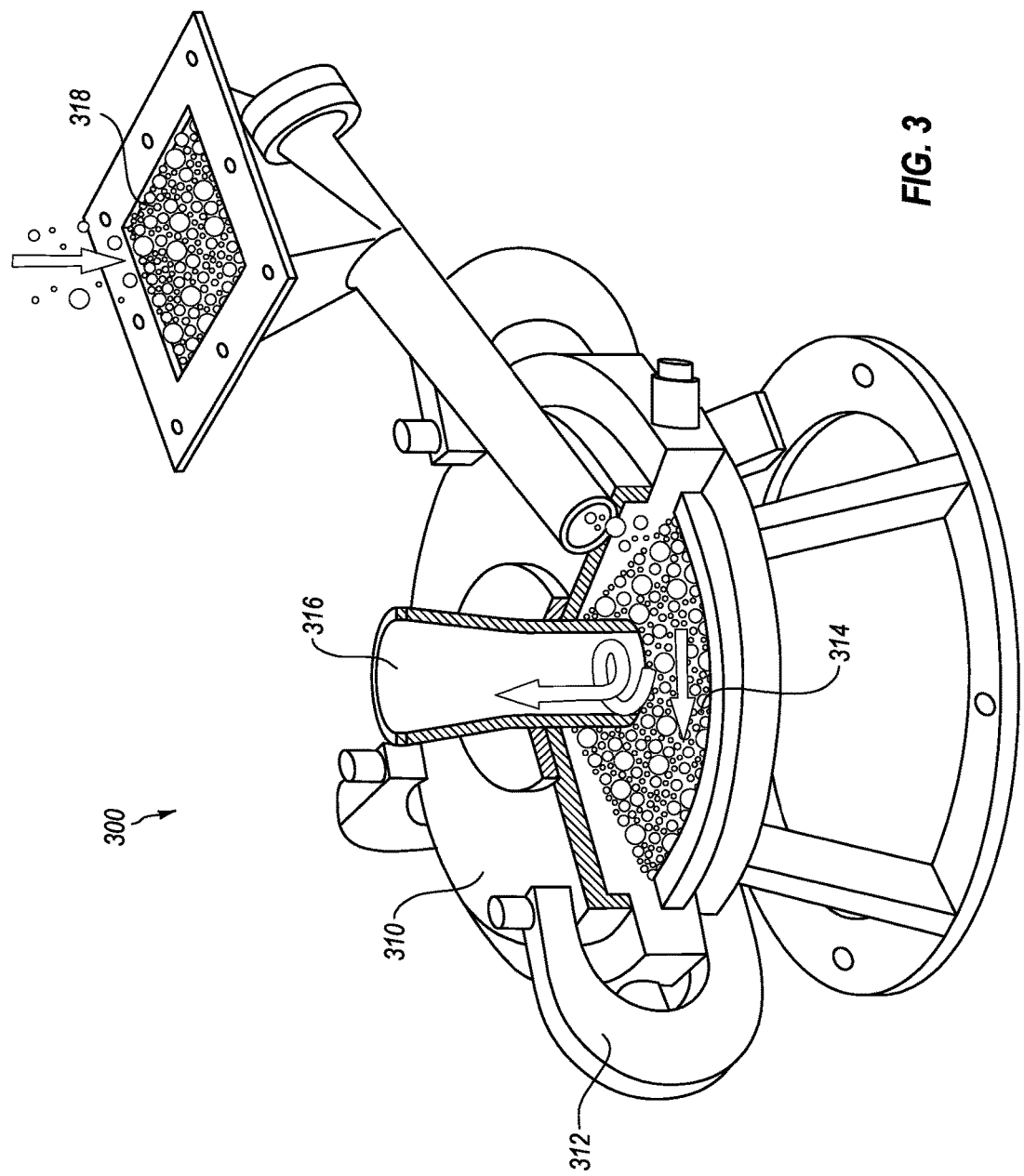
FIG. 3 illustrates a jet milling apparatus.

Milling apparatus for making particles as disclosed herein can be any mill suitable for fracturing a ceragenin compound to the desired particle size at the specified moisture content. FIG. 2 illustrates an example milling circuit 200 according to one embodiment of the invention. Milling circuit 200 includes a milling apparatus 210, feed material hopper 212, a fluid source 214, optionally a separator 216 and a product hopper 218.

Feed material is loaded into hopper 212, which is in fluid communication with milling apparatus 210. Particles from hopper 212 can be loaded into milling apparatus 212 by gravity feed, pneumatic pressure, or any other mechanism. If hopper 212 is used to store feed material for a significant amount of time it may be preferable to seal hopper 212 from outside moisture. Hopper 212 can also be used to introduce other materials such as desiccants, excipients, or grinding aids. Where more than one material is introduced, hopper 212 may also include a mixer to ensure homogeneity in the material fed to milling apparatus 210.

Fluid source 214 may be in fluid communication with hoper 212 and/or milling apparatus 210 to provide a fluid with a desired moisture content during milling. Fluid source 214 may be coupled to hopper 212 or milling apparatus 210 using known methods in the art such as a gas regulator.

Milling apparatus 210 can be a jet mill, ball mill, or other mill configured to produce particles less than 20 microns in size. The jet mill is typically configured to produce particle less than 20 microns by controlling the velocity of the particles in the mill. Ball mills can be configured to produce particles less than 20 microns by selecting a proper ball size. Those skilled in the art are familiar with configuring jet mills and ball mills to produce particles less than 20 microns, more preferably less than 10 microns, or 5 microns.

Optionally, milling system 200 may include separator 216, which may be external or internal to milling apparatus 210. Separator 216 classifies particles produced in milling apparatus 210 by size, and particles larger than the desired size are returned to milling apparatus 210 for further milling, and particles of desired size are collected as product. The use of a separator can produce particles with a narrow particle size distribution, which provides a more uniform particle size and can improve the mechanical properties of composites incorporating the ceragenin particulates.

In one embodiment, milling system 200 may include one or more moisture sensors on feed 212, fluid source 213, milling apparatus 210, separator 216, and/or product 218 to monitor the moisture content during fracturing.

FIG. 2 illustrates a jet milling apparatus 300 suitable for use in milling ceragenin compounds. FIG. 2 shows a portion of housing 310 removed to reveal a pulverizing chamber 312. In jet milling, pulverization takes place in chamber 312 as the feed material is driven at or near sonic velocity around the perimeter 314 by multiple jets of air. Typically grinding media is not required. Particle size reduction is the result of the high-velocity collisions between particles of the feed material itself.

The interior of chamber 312 may be designed to allow recirculation of over-sized particles, enhancing the incidence and the effect of these collisions. As particles are reduced in size and progressively lose mass, they naturally migrate toward the central discharge port 316, making precise classification both automatic and precisely controllable. Jet milling apparatus 300 is particularly suitable for ceragenins that must remain ultra-pure and those that are heat sensitive. Even cryogenic applications can be accommodated. Further, by precise metering of the product input and air or steam velocity, highly predictable and repeatable graduation and classification of the finished particles can be achieved.

IV. Method for Fracturing Ceragenins

Methods as disclosed herein relate to producing ceragenin particulates with a desired particle size using a milling apparatus and fracturing at proper moisture content. The proper moisture content during fracturing can be achieved by properly selecting the moisture content in the feed material, the moisture content of fluids in the milling apparatus during fracturing, and the moisture removed or added to the ceragenin particles as a consequence of any grinding aids, excipients, or desiccants present during fracturing. Heat generated during grinding may also affect moisture content.

One method for controlling moisture content during fracturing is to provide a feed material with a desirably low moisture content. The moisture content of the feed material is preferably less than 10%, 5%, or 1% by weight. Most ceragenins are naturally hygroscopic. Thus, the ceragenins must be dried and sealed from ambient humidity until just prior to use or dried at the time of use in order to maintain the desired moisture content.

In one embodiment, the ceragenin feed material may be milled in the presence of a dry gas. The dry gas may have a moisture content less than 10%, 5%, or 1% by weight. If the feed material has a higher moisture content than the dry gas, moisture will tend to be absorbed by the ceragenin compounds. While this occurrence is not desirable, it may be acceptable so long as the material being milled maintains a desired moisture content. In a preferred embodiment, the dry gas has a moisture content that is less than or equal to the moisture content of the feed material.

The ceragenin material may also be milled in the presence of an excipient or desiccant. The excipient or desiccant may be more hygroscopic than the feed material and/or have a moisture content that is substantially less than the moisture content of the feed material. Similarly to a dry gas, the excipient or desiccant may remove water weight from the ceragenin material. Optionally a desiccant may be used prior to milling to dry the ceragenin compound without introducing the desiccant into the milling apparatus.

V. Ceragenin Products

Particles produced from milling processes of the present invention can have a desired maximum or minimum average particle size, particle size distribution and/or particle morphology. Example of suitable particle sizes that have been found to give desired properties to composite materials include particles comminuted according to the methods of the present invention to have a particle size in a range from 5 nm to 20 microns, 100 nm to 15 microns, 500 nm to 10 microns, or 1 microns to 5 microns.

The particles can be milled to have monolithic particles or may be ground to smaller particles that agglomerate to form particles with a sub particle structure. The particles with a sub particle structure are highly advantageous to allow for the particles to be larger while still having dissolution properties more commensurate with smaller particles (i.e., because of the higher surface area of each sub particle). Where sub particles are present, the preferred particle size of the sub particles is less than 1 nm and the agglomerate particles are preferably greater than 1 micron, most preferably in a range of 1-20 microns, preferably 2-15 microns.

In some cases it may be desirable to provide the particles having a narrow particle size distribution. By comminuting the feed material using classification, the particle size distribution can be narrowed. In one embodiment, the narrowness of the distribution can be measured by d90/d10 and can less than 20, 15, 10, 7.5, 5, or 2.5.

Agglomeration of particles may be minimized by using a dispersant and/or minimizing the amount of moisture content.

The present invention also relates to composites that include ceragenin particulates manufactured according to the present invention. The ceragenin particulate may be incorporated into a polymeric material by polymerizing a precursor mixture including a polymerizable material and the ceragenin particles having a median particle size less than 20 microns, 15 microns, 10 microns, or 5 microns.

Figure 4:
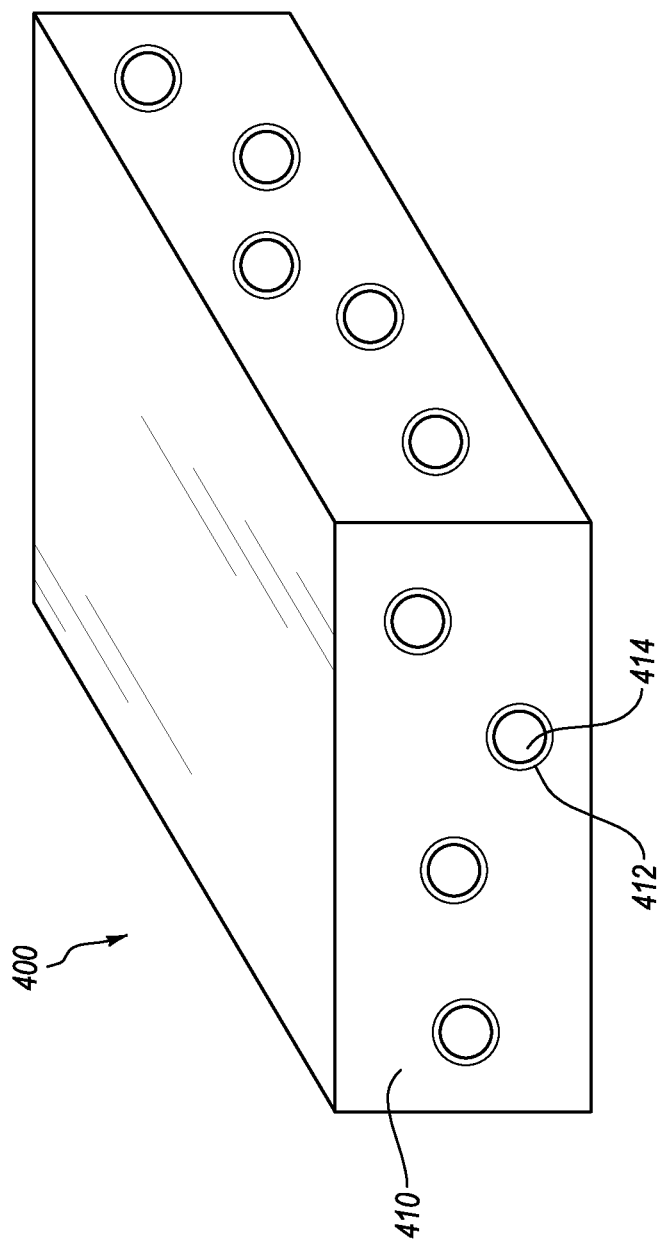
FIG. 4 illustrates a composite material including a polymeric material and a particulate ceragenin.

FIG. 4 illustrates a composite material 400 according to one embodiment of the present invention, which includes a polymeric matrix 410 and a plurality of ceragenin particles 412 that form voids 414 in continuous phase 412. Composite material 400 includes a composite matrix 410 and a quantity of ceragenin particles 412 dispersed throughout composite matrix 410. Composite matrix 410 can be fabricated from essentially any polymer material to provide a polymer structure into which ceragenin particles 412 may be dispersed. Ceragenin particles 412 are dispersed in composite matrix 410 such that ceragenin compounds contained therein may be eluted (i.e., dissolved) out of ceragenin particles 412 and composite material 400 when water or other aqueous fluids are brought into fluid contact with composite material 400.

The particular material used for the composite matrix will depend on the type of composite material being manufactured. Examples of suitable polymers include, but are not limited to, silicones, vinyls, urethanes, methacrylates, polyesters, thermoplastics, thermoplastic alloys, co-polymers, and the like. Polymers can be provided as monomers, precursors, prepolymers, oligomers, or polymers. Such monomers, precursors, prepolymers, oligomers, or polymers can be polymerized and/or cross-linked using techniques well-known in the art to make the polymer matrix of the composites described herein.

In a specific embodiment, composite material 400 may be prepared by mixing ceragenin particles that are dispersed in a dispersant into a suspension that contains a solvent and polydimethylsiloxane ("PDMS") polymer chains. The PDMS polymer chains may be catalytically cross-linked to form composite matrix 410.

Composite matrix 410 and ceragenin particles 412 together define voids 414 in composite material 400. Voids 414 are essentially formed in composite 400 by ceragenin particles 412. Ceragenin particles 412 dispersed in composite matrix 410 have an average particle and/or particle aggregate size in a range from 5 nanometers ("nm") to 40 micrometers ("µm"), 5 nm to 20 µm, 50 nm to 10 µm, 100 nm to 5 µm, or 1 µm to 10 µm. As a result, voids 414 created by inclusion of ceragenin particles 412 can have a size ranging from 5 nm to 40 µm, 5 nm to 20 µm, 50 nm to 10 µm, 100 nm to 5 µm, or 1 µm to 10 µm.

As a consequence of the small size of ceragenin particles 412 and their regular dispersion in composite material 400, composite matrix 410 is able to form a more-or-less continuous polymer structure around each of particles 412. This allows composite material 400 to have physical characteristics (e.g., hardness, tensile strength, elastomeric properties, etc.) that are similar to those that would be found in the polymer forming composite matrix 410 without ceragenin particles 412 dispersed therein.

In one embodiment, the composite material can include up to 35% (weight/weight) ("wt %") of ceragenin particles. In another embodiment, the composite material includes 1 wt % to 25 wt %, 16 wt % to 20 wt %, or 18 wt % ceragenin particles. It is believed that, because of the small size of the ceragenin particles, the composite material can include a large percentage of ceragenin particles while maintaining the physical characteristics of the composite matrix.

VI. Ceragenin Compounds

Example ceragenin compounds used to form ceragenin particles can have a formula as set forth in Formula (I):

(I)

[Chemical structure showing a four-ring system labeled A, B, C, D with substituents $R_1$ through $R_{18}$ and subscripts $m$, $n$, $p$, $q$]

where m, n, p, and q are independently 0 or 1; $R^1$-$R^{18}$ represent substituents that are attached to the indicated atom on the steroid backbone (i.e., steroid group); and at least two, preferably at least three, of $R^1$-$R^{18}$ each include a cationic group.

In one embodiment, rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, a substituted or unsubstituted aminoalkyl, a substituted or unsubstituted aryl, a substituted or unsubstituted arylaminoalkyl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, a substituted or unsubstituted C-carboxyalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, substituted or unsubstituted quaternaryammoniumalkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, substituted or unsubstituted hydroxyalkyl, substituted or unsubstituted alkyloxyalkyl, a substituted or unsubstituted aminoalkyl, a substituted or unsubstituted aryl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, and substituted or unsubstituted guanidinoalkylcarboxy, where $Q_5$ is a side chain of any amino acid, P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, substituted or unsubstituted alkylaminoalkylamino, substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a substituted or unsubstituted quaternaryammoniumalkylcarboxy, a substituted or unsubstituted di(alkyl)aminoalkyl, a substituted or unsubstituted C-carboxyalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, a substituted or unsubstituted guanidinoalkylcarboxy, or a pharmaceutically acceptable salt thereof.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$)alkyl, substituted or unsubstituted ($C_1$-$C_{18}$) alkyl amino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, a substituted or unsubstituted ($C_1$-$C_{18}$) aminoalkyl, a substituted or unsubstituted aryl, a substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkyloxy-($C_1$-$C_{18}$) alkyl, a substituted or unsubstituted ($C_1$-$C_{18}$) aminoalkylcarboxy, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted di($C_1$-$C_{18}$ alkyl)aminoalkyl, a substituted or unsubstituted C-carboxy($C_1$-$C_{18}$)alkyl, $H_2N$—$HC(Q_5)$-$C(O)$—O—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—O—, substituted or unsubstituted ($C_1$-$C_{18}$) guanidinoalkyloxy, substituted or unsubstituted ($C_1$-$C_{18}$) quaternaryammoniumalkylcarboxy, and substituted or unsubstituted ($C_1$-$C_{18}$) guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valence of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, a substituted or unsubstituted ($C_1$-$C_{18}$) aminoalkyl, a substituted or unsubstituted aryl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkylcarboxy, a substituted or unsubstituted ($C_1$-$C_{18}$) aminoalkylaminocarbonyl, di($C_1$-$C_{18}$ alkyl)aminoalkyl, a substituted or unsubstituted C-carboxy($C_1$-$C_{18}$)alkyl, $H_2N$—$HC(Q_5)$-$C(O)$—O—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—O—, substituted or unsubstituted ($C_1$-$C_{18}$) guanidinoalkyloxy, and substituted or unsubstituted ($C_1$-$C_{18}$) guanidinoalkylcarboxy, where $Q_5$ is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxyamido, a substituted or unsubstituted ($C_1$-$C_{18}$) quaternaryammoniumalkylcarboxy, substituted or unsubstituted di($C_1$-$C_{18}$ alkyl) aminoalkyl, a substituted or unsubstituted C-carboxy($C_1$-$C_{18}$)alkyl, $H_2N$—$HC(Q_5)$-$C(O)$—O—, $H_2N$—$HC(Q_5)$-$C(O)$—N(H)—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—O—, substituted or unsubstituted ($C_1$-$C_{18}$) guanidinoalkyloxy, a substituted or unsubstituted ($C_1$-$C_{18}$) guanidinoalkylcarboxy, or a pharmaceutically acceptable salt thereof.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkyl carboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkyl amino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) amino alkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkyl amino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, unsubstituted ($C_1$-$C_{18}$) guanidinoalkyl carboxy, or a pharmaceutically acceptable salt thereof.

According to other embodiments, ceragenin compounds used to make particles as disclosed can have a structure as shown in Formula (II), which is closely related to, but not identical to, Formula (I):

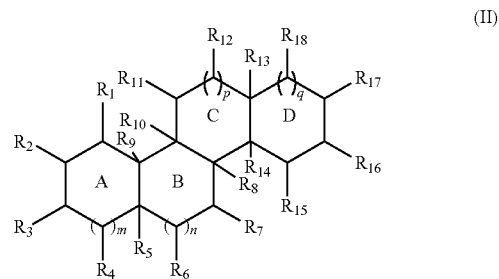

where each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1 (i.e., each ring may independently be 5-membered or 6-membered); each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkyl amino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—$HC(Q_5)$-$C(O)$—O—, $H_2N$—$HC(Q_5)$-$C(O)$—N(H)—, ($C_1$-$C_{10}$) azidoalkyloxy, ($C_1$-$C_{10}$) cyanoalkyloxy, P.G.-HN—$HC(Q_5)$-$C(O)$—O—, ($C_1$-$C_{10}$) guanidinoalkyloxy, ($C_1$-$C_{10}$) quaternaryammoniumalkylcarboxy, and ($C_1$-$C_{10}$) guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ may be independently deleted when one of fused rings A, B, C, or D is unsaturated so as to complete the valency of the carbon atom at that site, or selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, a substituted or unsubstituted $(C_1-C_{10})$ aminoalkyl, a substituted or unsubstituted aryl, $(C_1-C_{10})$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkylcarboxy, a substituted or unsubstituted $(C_1-C_{10})$ aminoalkylaminocarbonyl, $H_2N-HC(Q_5)-C(O)-O-$, $H_2N-HC(Q_5)-C(O)-N(H)-$, $(C_1-C_{10})$ azidoalkyloxy, $(C_1-C_{10})$ cyanoalkyloxy, P.G.-HN-HC($Q_5$)-C(O)-O-, $(C_1-C_{10})$ guanidinoalkyloxy, and $(C_1-C_{10})$ guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted $(C_1-C_{10})$ aminoalkyl, a substituted or unsubstituted $(C_1-C_{10})$ aminoalkyloxy, $(C_1-C_{10})$ alkylcarboxy-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkylcarboxy, a substituted or unsubstituted arylamino $(C_1-C_{10})$ alkyl, a substituted or unsubstituted $(C_1-C_{10})$ amino alkyloxy-$(C_1-C_{10})$ aminoalkylaminocarbonyl, a substituted or unsubstituted $(C_1-C_{10})$ aminoalkylaminocarbonyl, a substituted or unsubstituted $(C_1-C_5)$ aminoalkylcarboxyamido, a $(C_1-C_{10})$ quaternaryammonium alkylcarboxy, $H_2N-HC(Q_5)-C(O)-O-$, $H_2N-HC(Q_5)-C(O)-N(H)-$, $(C_1-C_{10})$ azidoalkyloxy, $(C_1-C_{10})$ cyanoalkyloxy, P.G.-HN-HC($Q_5$)-C(O)-O-, $(C_1-C_{10})$ guanidinoalkyloxy, a $(C_1-C_{10})$ guanidinoalkylcarboxy, or a pharmaceutically acceptable salt thereof.

In Formula (II), at least two or three of $R_3$, $R_7$, or $R_{12}$ may independently include a cationic moiety attached to the Formula (II) structure via a hydrolysable linkage. Optionally, a tail moiety may be attached to Formula (II) at $R_{17}$. The tail moiety may be charged, uncharged, polar, nonpolar, hydrophobic, amphipathic, and the like. Although not required, at least two or three of m, n, p. and q are 1. In a preferred embodiment, m, n, and p=1 and q=0. Examples of such structures are shown in FIGS. 1A-1B.

In some embodiments, ceragenin compounds can be represented by Formula (III):

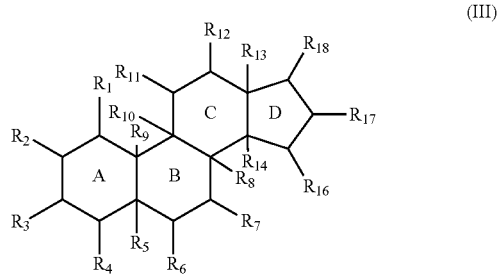

(III)

In some embodiments, rings A, B, C, and D are independently saturated.

In some embodiments, one or more of rings A, B, C, and D are heterocyclic.

In some embodiments, rings A, B, C, and D are non-heterocyclic.

In some embodiments, $R_3$, $R_7$, $R_{12}$, and $R_{18}$ are independently selected from the group consisting of hydrogen, an unsubstituted $(C_1-C_{18})$ alkyl, unsubstituted $(C_1-C_{18})$ hydroxyalkyl, unsubstituted $(C_1-C_{18})$ alkyloxy-$(C_1-C_{18})$ alkyl, unsubstituted $(C_1-C_{18})$ alkylcarboxy-$(C_1-C_{18})$ alkyl, unsubstituted $(C_1-C_{18})$ alkylamino-$(C_1-C_{18})$alkyl, unsubstituted $(C_1-C_{18})$ alkylamino-$(C_1-C_{18})$ alkylamino, unsubstituted $(C_1-C_{18})$ alkylamino-$(C_1-C_{18})$ alkylamino-$(C_1-C_{18})$ alkylamino, an unsubstituted $(C_1-C_{18})$ amino alkyl, an unsubstituted arylamino-$(C_1-C_{18})$ alkyl, an unsubstituted $(C_1-C_{18})$ amino alkyloxy, an unsubstituted $(C_1-C_{18})$ amino alkyloxy-$(C_1-C_{18})$ alkyl, an unsubstituted $(C_1-C_{18})$ amino alkylcarboxy, an unsubstituted $(C_1-C_{18})$ aminoalkylaminocarbonyl, an unsubstituted $(C_1-C_{18})$ aminoalkylcarboxamido, an unsubstituted di($C_1-C_{18}$ alkyl)amino alkyl, unsubstituted $(C_1-C_{18})$ guanidinoalkyloxy, unsubstituted $(C_1-C_{18})$ quaternaryammoniumalkylcarboxy, and unsubstituted $(C_1-C_{18})$ guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted $(C_1-C_6)$ alkyl.

In some embodiments, $R_3$, $R_7$, $R_{12}$, and $R_{18}$ are independently selected from the group consisting of hydrogen, an unsubstituted $(C_1-C_6)$ alkyl, unsubstituted $(C_1-C_6)$ hydroxyalkyl, unsubstituted $(C_1-C_{16})$ alkyloxy-$(C_1-C_5)$ alkyl, unsubstituted $(C_1-C_{16})$ alkylcarboxy-$(C_1-C_5)$ alkyl, unsubstituted $(C_1-C_{16})$ alkylamino-$(C_1-C_5)$alkyl, unsubstituted $(C_1-C_{16})$ alkylamino-$(C_1-C_5)$ alkylamino, unsubstituted $(C_1-C_{16})$ alkylamino-$(C_1-C_{16})$ alkylamino-$(C_1-C_5)$ alkylamino, an unsubstituted $(C_1-C_{16})$ aminoalkyl, an unsubstituted arylamino-$(C_1-C_5)$ alkyl, an unsubstituted $(C_1-C_5)$ aminoalkyloxy, an unsubstituted $(C_1-C_{16})$ aminoalkyloxy-$(C_1-C_5)$ alkyl, an unsubstituted $(C_1-C_5)$ aminoalkylcarboxy, an unsubstituted $(C_1-C_5)$ aminoalkylaminocarbonyl, an unsubstituted $(C_1-C_5)$ amino alkylcarboxamido, an unsubstituted di($C_1-C_5$ alkyl)amino-$(C_1-C_5)$ alkyl, unsubstituted $(C_1-C_5)$ guanidinoalkyloxy, unsubstituted $(C_1-C_{16})$ quaternaryammoniumalkylcarboxy, and unsubstituted $(C_1-C_{16})$ guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkoxycarbonylalkyl; and alkylcarboxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_3$, $R_7$, and $R_{12}$ are aminoalkyl-carboxy.

In some embodiments, $R_{18}$ is alkylaminoalkyl.

In some embodiments, $R_{18}$ is alkoxycarbonylalkyl.

In some embodiments, $R_{18}$ is di(alkyl)aminoalkyl.

In some embodiments, $R_{18}$ is alkylcarboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, m, n, and p are each 1 and q is 0.

In some embodiments, ceragenin compounds can be represented by Formula (IV):

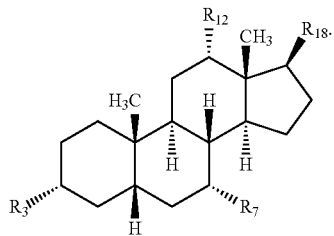

In some embodiments, the CSA, or a pharmaceutically acceptable salt thereof, is:

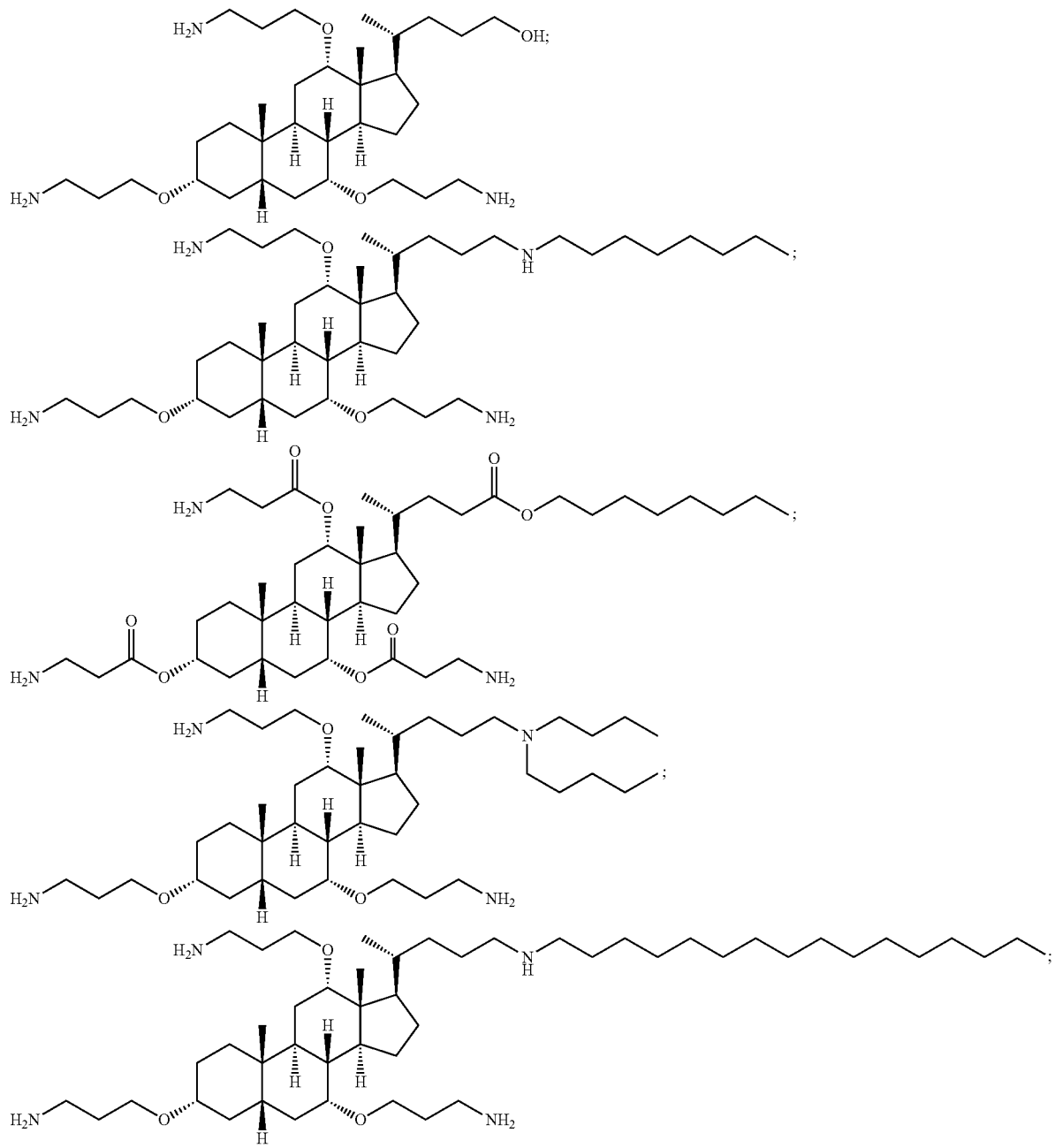

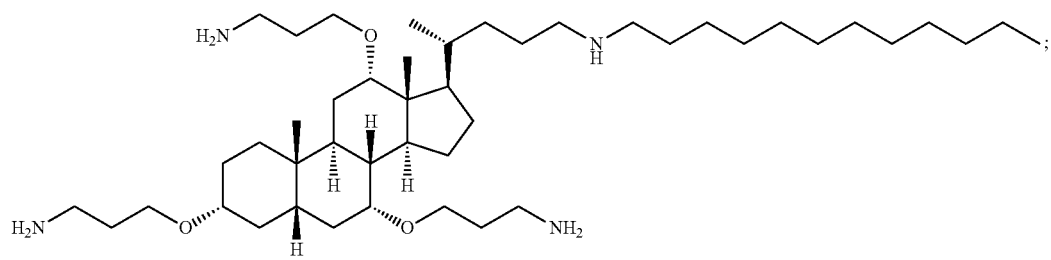
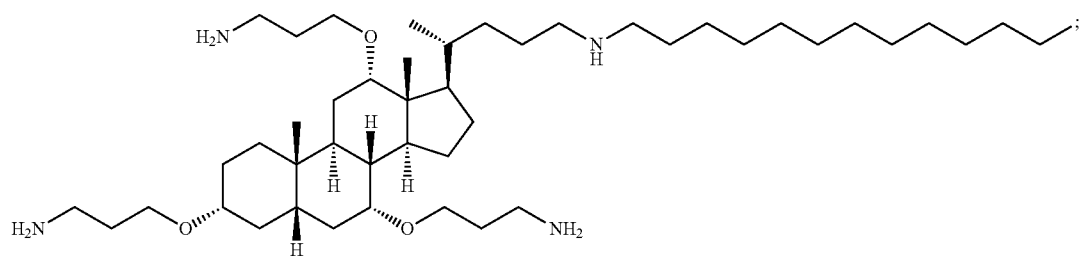
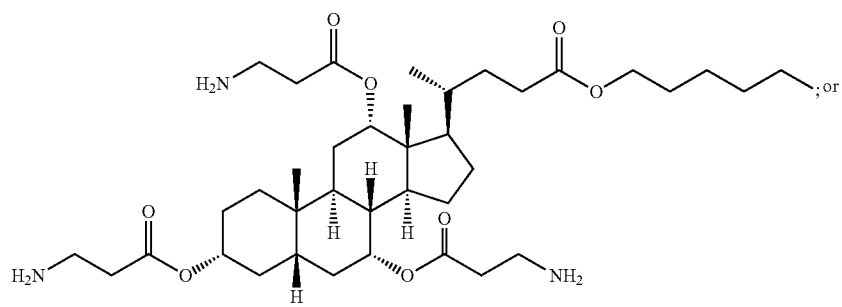
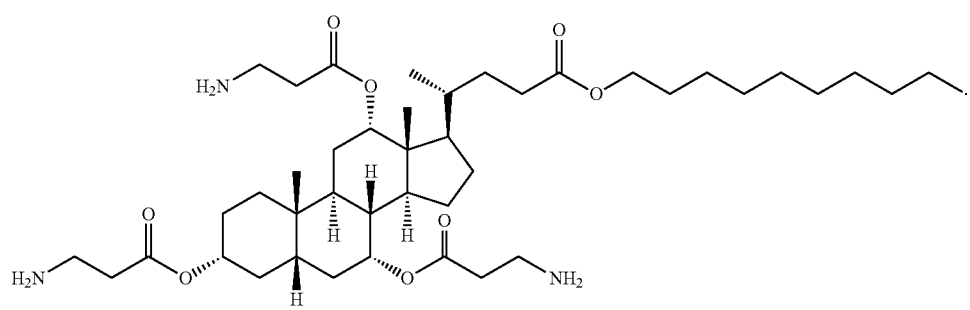
In some embodiments, the ceragenin compound is
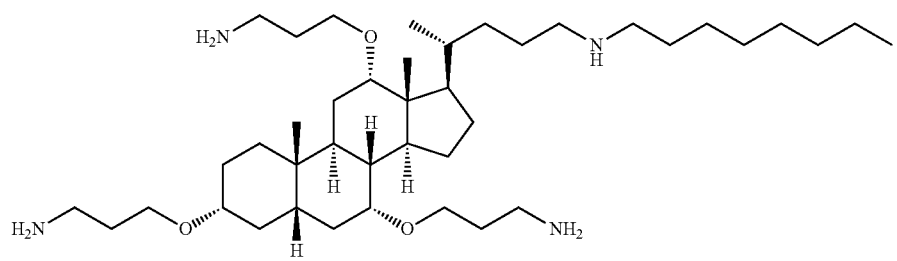

In other embodiments, the ceragenin compound is

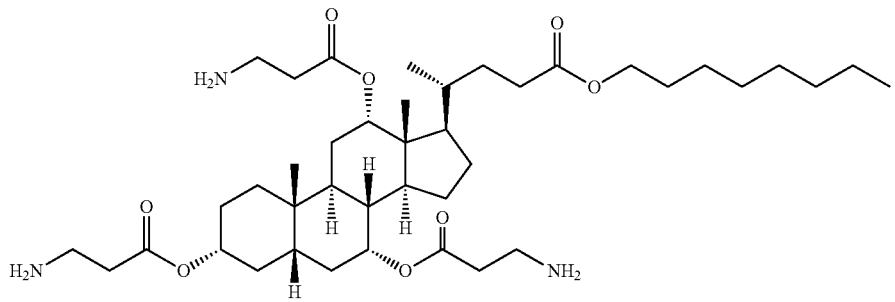

In other embodiments, the ceragenin compound is

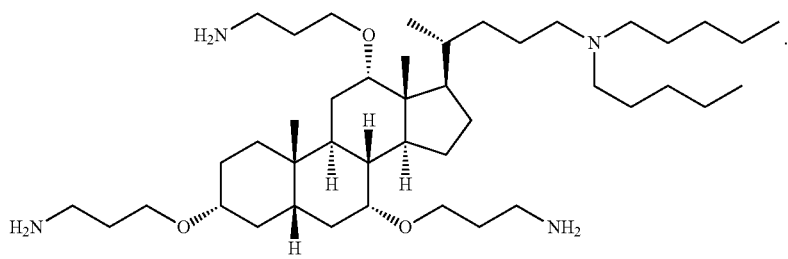

In other embodiments, the ceragenin compound is

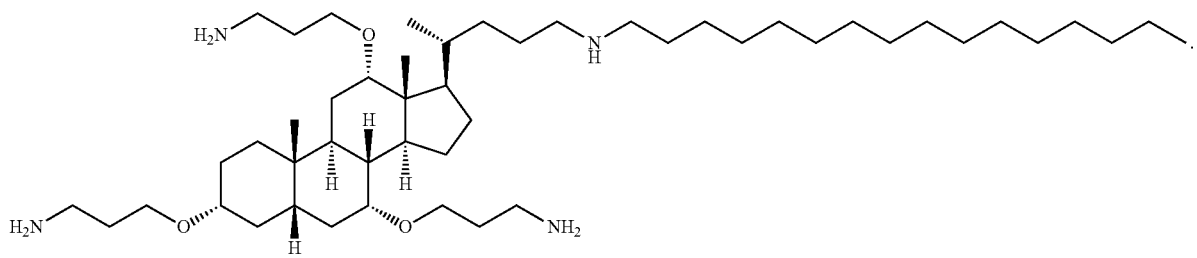

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ represent substituents that can be attached to the indicated atom. Unless otherwise specified, an R group may be substituted or unsubstituted.

The term "ring" as used herein can be heterocyclic or carbocyclic. The term "saturated" used herein refers to the fused ring of Formula (II) having each atom in the fused ring either hydrogenated or substituted such that the valency of each atom is filled. The term "unsaturated" used herein refers to the fused ring of Formula (II) where the valency of each atom of the fused ring may not be filled with hydrogen or other substituents. For example, adjacent carbon atoms in the fused ring can be doubly bound to each other. Unsaturation can also include deleting at least one of the following pairs and completing the valence of the ring carbon atoms at these deleted positions with a double bond; such as $R_5$ and $R_9$; $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R^aO(CH_2)_mO—$, $R^b(CH_2)_nO—$, $R^cC(O)O(CH_2)_pO—$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3—$, $CH_3CH_2—$, $CH_3CH_2CH_2—$, $(CH_3)_2CH—$, $CH_3CH_2CH_2CH_2—$, $CH_3CH_2CH(CH_3)—$ and $(CH_3)_3C—$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms "alkyl" and "alkoxy" defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a OH group.

A "cyano" group refers to a "—CN" group.

A "carbonyl" or an "oxo" group refers to a C=O group.

The term "azido" as used herein refers to a —N3 group.

As used herein, "aminoalkyl" refers to an amino group connected, as a substituent, via a lower alkylene group. Examples include H$_2$N-alkyl- with the term "alkyl" defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term "alkyl" as defined herein.

As used herein, "alkylaminoalkyl" refers to an alkyl group connected, as a substituent, to an amino group that is connected, as a substituent, to an alkyl group. Examples include alkyl-NH-alkyl-, with the term "alkyl" as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

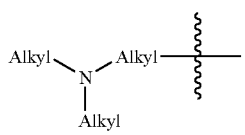

with the term "alkyl" as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term "alkyl" as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term "alkyl" as defined herein.

As used herein, "arylaminoalkyl" refers to an aryl group connected, as a substituent, to an amino group that is connected, as a substituent, to an alkyl group. Examples include aryl-NH-alkyl-, with the terms "aryl" and "alkyl" as defined herein.

As used herein, "aminoalkyloxy" refers to an amino group connected, as a substituent, to an alkyloxy group. Examples include H$_2$N-alkyl-O— and H$_2$N-alkoxy- with the terms "alkyl" and "alkoxy" as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms "alkyl" and "alkoxy" as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term "alkyl" as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term "alkyl" as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term "alkyl" as defined herein.

As used herein, "azidoalkyloxy" refers to an azido group connected as a substituent, to an alkyloxy group. Examples include N$_3$-alkyl-O— and N$_3$-alkoxy- with the terms "alkyl" and "alkoxy" as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

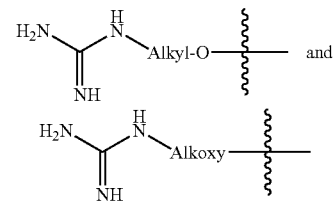

with the terms "alkyl" and "alkoxy" as defined herein.

As used herein, "guanidinoalkylcarboxy" refers to a guanidinyl group connected, as a substituent, to an alkyl group connected, as a substituent, to a carboxy group. Examples include

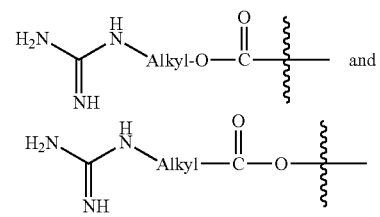

with the term "alkyl" as defined herein.

As used herein, "quaternaryammoniumalkylcarboxy" refers to a quaternized amino group connected, as a substituent, to an alkyl group connected, as a substituent, to a carboxy group. Examples include

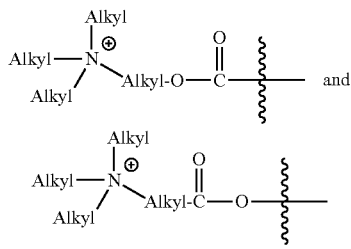

with the term "alkyl" as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is $(C_1\text{-}C_{10})$ alkyloxy-$(C_1\text{-}C_{10})$ alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

Ceragenin compounds include, but are not limited to, compounds having cationic groups (e.g., amine or guanidine groups) covalently attached to a steroid backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from any one or more of positions $R_3$, $R_7$, and $R_{12}$ of the sterol backbone.

Anti-microbial CSA compounds described herein may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$ of Formula (II). A tail moiety may include the heteroatom (O or N) covalently coupled to the sterol backbone.

The tail moiety may, for example, be configured to alter the hydrophobicity/hydrophilicity of the ceragenin compound. Ceragenin compounds of the present disclosure having different degrees of hydrophobicity/hydrophilicity may, for example, have different rates of uptake into different target microbes. Likewise, altering the hydrophobicity/hydrophilicity of the ceragenin compounds described herein may affect the retention of the ceragenin compounds in certain media.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

As used in this specification and the appended claims, the singular forms "a", "an", and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for making a fine ceragenin particulate material, comprising:
providing a ceragenin feed material comprised of ceragenin molecules, each having a sterol backbone and a plurality of cationic groups attached thereto, the ceragenin feed material comprising particles having a size between 20 µm and 0.5 mm and having a moisture content of less than or equal to 10% by weight; and
fracturing the individual particles of the ceragenin feed material in a milling apparatus to produce individual fractured ceragenin particles of reduced size, the ceragenin particles of reduced size comprising ceragenin subparticles and agglomerates of the ceragenin subparticles, the ceragenin subparticles having an average particle size less than 1 µm, and the agglomerates having a particle size distribution with a median particle size in a range of 5 nm 1 urn to 20 µm.

2. The method as in claim 1, wherein when providing a ceragenin feed material, the ceragenin feed material has a moisture content of less than or equal to 5% by weight.

3. The method as in claim 1, wherein when providing a ceragenin feed material, the ceragenin feed material has a moisture content of less than or equal to 1% by weight.

4. The method as in claim 1, wherein the milling apparatus fluidizes coarse ceragenin material using a fluidizing gas and the fluidizing gas has a moisture content sufficiently low to prevent the fluidizing gas from increasing the moisture content of the ceragenin feed material to a moisture content greater than 10% by weight.

5. The method as in claim 4, wherein the fluidizing gas is nitrogen or dry air.

6. The method as in claim 1, further comprising drying the ceragenin feed material to reduce the moisture content prior to introducing the ceragenin feed material into the milling apparatus.

7. The method as in claim 1, further comprising milling the ceragenin feed material in the presence of a grinding aid selected from desiccants and excipients.

8. The method as in claim 7, wherein the desiccant or excipient is selected from the group consisting of lactate, citrate, magnesium stearate, calcium chloride, and potassium carbonate.

9. The method as in claim 1, wherein the median particle size of the agglomerates is in a range of 1 micron to 15 microns.

10. The method as in claim 1, wherein the median particle size of the agglomerates is in a range of 1 micron to 10 microns.

11. The method as in claim 1, wherein the median particle size of the agglomerates is in a range of 1 µm to 5 µm.

12. The method as in claim 1, wherein the milling apparatus is a jet mill, a ball mill, a high pressure vertical roller mill, or a high pressure horizontal mill.

13. The method as in claim 1, wherein the fracturing is carried out from high velocity collisions of ceragenin particles.

14. The method as in claim 1, wherein the fracturing produces a narrow particle size distribution with an upper end point (UEP) to lower end point (LEP) ratio of less than or equal to 20, wherein the UEP is the d90 and the LEP is the d10 of the particle size distribution of the particulate ceragenin.

15. The method as in claim 14, wherein the fracturing includes producing an intermediate ceragenin particulate material and classifying the intermediate ceragenin particulate material to produce fine particulate ceragenin and a coarse intermediate fraction, the method further comprising recirculating the coarse intermediate fraction to the milling apparatus for additional fracturing.

16. The method as in claim 15, wherein the percentage of recirculated intermediate ceragenin particulate material is at least 10%, by weight of the intermediate ceragenin particulate material.

17. The method as in claim 15, wherein the intermediate ceragenin particulate material is classified using a high efficiency cyclone separator.

18. A method for making a fine ceragenin particulate material from a coarse ceragenin feed material, comprising:
providing a coarse ceragenin feed material comprised of ceragenin molecules, each having a sterol backbone and a plurality of cationic groups attached thereto, the coarse ceragenin feed material having a particle size of at least 100 µm and a moisture content of less than or equal to 10% by weight; and
fracturing the coarse ceragenin feed material in a milling apparatus to produce ceragenin particles of reduced size and having a particle size distribution with a median particle size in a range of 5 nm to 1 µm.

19. A method for making a fine ceragenin particulate material from a coarse ceragenin feed material, comprising:
providing a coarse ceragenin feed material comprised of ceragenin molecules, each having a sterol backbone and a plurality of cationic groups attached thereto, the coarse ceragenin feed material having a particle size of at least 20 µm and a moisture content of less than or equal to 10% by weight; and
jet milling the coarse ceragenin feed material in a jet milling apparatus to produce ceragenin particles of reduced size and having a particle size distribution with a median particle size in a range of 5 nm to 10 µm, wherein the jet milling includes producing an intermediate ceragenin particulate material and classifying the intermediate ceragenin particulate material to produce fine particulate ceragenin and a coarse intermediate fraction, the method further comprising recirculating the coarse intermediate fraction to the milling apparatus for additional fracturing.

\* \* \* \* \*